US008227442B2

(12) United States Patent
Rossi et al.

(10) Patent No.: US 8,227,442 B2
(45) Date of Patent: *Jul. 24, 2012

(54) NUCLEOLAR TARGETING OF THERAPEUTICS AGAINST HIV

(75) Inventors: John J. Rossi, Rancho Cucamonga, CA (US); Alessandro Michienzi, Rome (IT)

(73) Assignee: City of Hope, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/835,333

(22) Filed: Jul. 13, 2010

(65) Prior Publication Data

US 2011/0046208 A1 Feb. 24, 2011

Related U.S. Application Data

(60) Continuation of application No. 10/902,145, filed on Jul. 30, 2004, now abandoned, which is a division of application No. 09/864,873, filed on May 25, 2001, now Pat. No. 6,995,258.

(60) Provisional application No. 60/206,976, filed on May 25, 2000.

(51) Int. Cl.
*C12N 15/11* (2006.01)
*C07H 21/04* (2006.01)

(52) U.S. Cl. ..................... 514/44 A; 536/24.5

(58) Field of Classification Search ................. 435/6.91, 435/31, 91.1, 455; 514/44, 44 A; 536/23.1, 536/24.5

See application file for complete search history.

(56) References Cited

U.S. PATENT DOCUMENTS

| 5,736,294 | A | * | 4/1998 | Ecker et al. ................... 435/375 |
| 5,942,395 | A | * | 8/1999 | Fournier et al. ............... 435/6.16 |
| 6,069,007 | A | | 5/2000 | Rossi et al. |
| 6,740,750 | B1 | * | 5/2004 | Taira et al. ................... 536/24.5 |
| 6,995,258 | B1 | * | 2/2006 | Rossi et al. ................... 536/24.5 |

FOREIGN PATENT DOCUMENTS

| JP | 200069972 | | 3/2000 |
| WO | WO 99/67400 | * | 12/1999 |

OTHER PUBLICATIONS

Samarsky et al, EMBO J., vol. 17, No. 13, pp. 3747-3757 (1998).*
Samarsky et al., Proc. Natl. Acad. Sci., vol. 96, pp. 6609-6614 (1999).*
Sullenger et al., J. Virol., vol. 65, No. 12, pp. 6811-6816 (1998).*
Marasco et al. Arch Virol. 1994; 139: 133-54.*
Browning et al., "Potent Inhibition of Human Immunodeficiency Virus Type 1 (HIV-1) Gene Expression and Virus Production by an HIV-2 Tat Activation-Response RNA Decoy" J. Virol 73(6):5191-5195, 1999.
Buonomo et al., "The Rev protein is able to transport to the cytoplasm small nucleolar RNAs containing a Rev binding element" RNA 5:993-1002, 1999.
Caffarelli et al., "In Vivo Identification of Nuclear Factors Interacting with the Conserved Elements of Box C/D Small Nucleolar RNAs" Mol. Cell Biol. 18(2):1023-1028, 1998.
Cagnon et al., "Protection of a T-Cell Line from Human Immunodeficiency Virus Replication by the Stable Expression of a Short Antisense RNA Sequence Carried by a Shuttle RNA Molecule" J. Acquir. Immune Defic. Syndr. Hum. Retrovirol. 9:349-358, 1995.
Cagnon et al., "Retroviral Delivery and Anti-HiV Testing of Hammerhead Ribozymes" Methods in Molecular Biology 74:451-457, 1997.
Churcher et al., "The RNA element encoded by the trans-activation-responsive region of human immunodeficiency virus type 1 is functional when displaced downstream of the start of transcription" Proc. Natl. Acad. Sci. USA 92:2408-2412, 1995.
Cullen et al., "Subcellular Localization of the Human Immunodeficiency Virus trans-Acting art Gene Product" J. Virol. 62:2498-2501, 1988.
Dayton et al., "The Trans-Activator Gene of the Human T Cell Lymphotropic Virus Type III Is Required for Replication" Cell 44:941-947, 1986.
Dingwall et al., "Human immunodeficiency virus 1 tat protein binds trans-activation-responsive region (TAR) RNA in vitro" Proc. Natl. Acad. Sci. USA 86:6925-6929, 1989.
Feng et al., "HIV-1 tat trans-activation requires the loop sequence within tar" Nature (London) 334:165-167, 1988.
Fisher et al., "The trans-activator gene of HTLV-III is essential for virus replication" Nature 320:367-371, 1986.
Fragapane et al., "A novel small nucleolar RNA (U16) is encoded inside a ribosomal protein intron and originates by processing of the pre-mRNA" EMBO J. 12(7):2921-2928, 1993.
Gait et al., "RNA recognition by the human immuno-deficiency virus Tat and Rev proteins" Trends in Biochem. Sci. 18:255-259, 1993.
Good et al., "Expression of small, therapeutic RNAs in human cell nuclei" Gene Ther. 4:45-54, 1997.
Gorse et al., "Antibody to Native Human Immunodeficiency Virus Type 1 Envelope Glycoproteins Induced by HIB and MN Recombinant gp120 Vaccines" Clinical and Diagnostic Laboratory Immunology 3(4):378-386, 1996.

(Continued)

*Primary Examiner* — Brian Whiteman
(74) *Attorney, Agent, or Firm* — Rothwell, Figg, Ernst & Manbeck, P.C.

(57) ABSTRACT

The HIV regulatory proteins Tat and Rev accumulate in nucleoli of human cells. No functional role has been attributed to this localization. Recently it was demonstrated that expression of Rev induces nucleolar re-localization of some nuclear factors involved in Rev export. Thus, it is likely that the nucleolus plays a critical role in Rev-mediated export of singly spliced and unspliced HIV-1 RNAs. As a test for trafficking of HIV-1 RNAs into the nucleolus, a hammerhead ribozyme which specifically cleaves HIV-1 RNA was joined to the U16 snoRNA resulting in accumulation of the ribozyme within nucleoli of human cells. Stably transduced human T-cells expressing this nucleolar localized ribozyme dramatically suppressed HIV-1 replication, confirming a possible trafficking of the HIV RNA through the nucleoli of human cells. In addition, a TAR element which binds Tat was joined to the U16 snoRNA, also resulting in localization in the nucleoli and inhibiting HIV replication.

18 Claims, 14 Drawing Sheets
(6 of 14 Drawing Sheet(s) Filed in Color)

OTHER PUBLICATIONS

Haseloff et al., "Simple RNA enzymes with new and highly specific endoribonuclease activities" Nature 334:585-591, 1988.

Hertel et al., "Numbering system for the hammerhead" Nucleic Acids Res. 20(12):3252, 1992.

Kalland et al., "Rex-Dependent Nucleolar Accumulation of HTLV-1 mRNAs" The New Biologist 3(4):389-397, 1991.

Konopka et al., "Receptor Ligand-Facilitated Cationic Liposome Delivery of Anti-HIV-1 Rev-Binding Aptamer and Ribozyme DNAs" J. Drug Targeting 5(4):247-259, 1998.

Lafontaine et al., "Birth of the snoRNPs: the evolution of the modification-guide snoRNAs" Trends in Biochem. Sci. 23:383-388, 1998.

Lange et al., "Conserved Boxes C and D are essential nucleolar localization elements of U14 and U8 snoRNAs" EMBO J. 17(11):3176-3187, 1998.

Lee et al., "mRNA localization signals can enhance the intracellular effectiveness of hammerhead ribozymes" RNA 5:1200-1209, 1999.

Michienzi et al., "Ribozyme-mediated inhibition of HIV 1 suggests nucleolar trafficking of HIV-1 RNA" PNAS 97 (16):8955-8960, 2000.

Michienzi et al., "A chimeric nucleolar Rev decoy inhibits the HIV replication" Nucleic Acids Symposium Series 41:211-214, 1999.

Michienzi et al., "Inhibition of Human Immunodeficiency Virus Type 1 Replication by Nuclear Chimeric Anti-HIV Ribozymes in a Human T Lymphoblastoid Cell Line" Hum. Gene Ther. 9:621-628, 1998.

Muesing et al., "Regulation of mRNA Accumulation by a Human Immunodeficiency Virus Trans-Activator Protein" Cell 48:691-701, 1987.

Müller et al., "Stimulation of HIV-1 neutralizing antibodies in simian HIV-IIIB-infected macaques" Proc. Natl. Acad. Sci. USA 9:276-281, 1998.

Ojwang et al., "Inhibition of human immunodeficiency virus type 1 expression by a hairpin ribozyme" Proc. Natl. Acad. Sci. USA 89:10802-10806, 1992.

Pederson, "Survey and Summary, The plurifunctional nucleolus" Nucleic Acids Res. 26(17):3871-3876, 1998.

Prislei et al., "Use of adenoviral VAI small RNA as a carrier for cytoplasmic delivery of ribozymes" RNA 3:677-687, 1997.

Prislei et al., "Two different snoRNAs are encoded in introns of amphibian and human L1 ribosdomal protein genes" Acids Res. 21(25):5824-5830, 1993.

Ratner et al., "Complete nucleotide sequence of the AIDS virus, HTLV-III" Nature 313:277-284, 1985.

Rosen et al., "The Location of Cis-Acting Regulatory Sequences in the Human T Cell Lymphotropic Virus Type III (HTLV-III/LAV) Long Terminal Repeat" Cell 41:813-823, 1985.

Rossi, "Ribozymes in the Nucleolus" Science 285:1685, 1999.

Rossi, "Ribozymes, genomics and therapeutics" Chemistry & Biology 6:R33-37, 1999.

Ruffner et al., "Sequence Requirements of the Hammerhead RNA Self-Cleavage Reaction" Biochemistry 29:10695-10702, 1990.

Samarsky et al., "The snoRNA box D/D motif directs nucleolar targeting and also couples snoRNA synthesis and localization" EMBO J. 17(13):3747-3757, 1998.

Samarsky et al., "A small nucleolar RNA:ribozyme hybrid cleaves a nucleolar RNA target in vivo with near-perfect efficiency" Proc. Natl. Acad. Sci. USA 96:6609-6614, 1999.

Sheline et al., "Two distinct nuclear transcription factors recognize loop and bulge residues of the HIV-1 TAR RNA hairpin" Genes & Development 5:2508-2520, 1991.

Siomi et al., "Sequence Requirements for Nucleolar Localization of Human T Cell Leukemia Virus Type I pX protein, Which Regulates Viral RNA Processing," Cell 55:197-209, 1988.

Stauber et al., "Intracellular Trafficking and Interactions of the HIV-1 Tat Protein" Virology 252:126-136, 1998.

Sullenger et al., "Analysis of trans-Acting Response Decoy RNA-Mediated Inhibition of Human Immunodeficiency Virus Type 1 Transactivation," J. Virol. 65(12):6811-6816, 1991.

Sullenger et al., "Tethering Ribozymes to a Retroviral Packaging Signal for Destruction of Viral RNA" Science 262:1566-1569, 1993.

Uhlenbeck, "A small catalytic oligoribonucleotide" Nature 328:596-600, 1987.

Weinstein et al., "Guided tours: from precursor snoRNA to functional snoRNP" Curr. Opin. Cell Biol. 11:378-384, 1999.

Wu et al., "tat regulates binding of the of the human immunodeficiency virus trans-activating region RNA loop-binding protein TRP-185" Genes & Development 5:2128-2140, 1991.

Lang et al. "Conserved Boxes C and D are essential nucleolar localization elements of U14 and U8 snoRNAs" EMBO J. 17(11):3176-3187, 1998.

Michienzi et al. "A chimeric nucleolar Rev decoy inhibits the HIV replication" Nucl. Acids Symp. 41:211-214, 1999.

Samarsky et al. "The snoRNA box C/D motif directs nucleolar targeting and also couples snoRNA synthesis and localization" EMBO J. 17(13):3747-3757, 1998.

Lee, et al. "Overexpression of RRE-Derived Sequences Inhibits HIV-1 Replication in CEM Cells" The New Biologist, 4 (1):66-74, 1992.

Sullenger, et al. "Overexpression of TAR Sequences Renders Cells Resistant to Human Immunodeficiency Virus Replication" Cell, 63:601-608, 1990.

\* cited by examiner

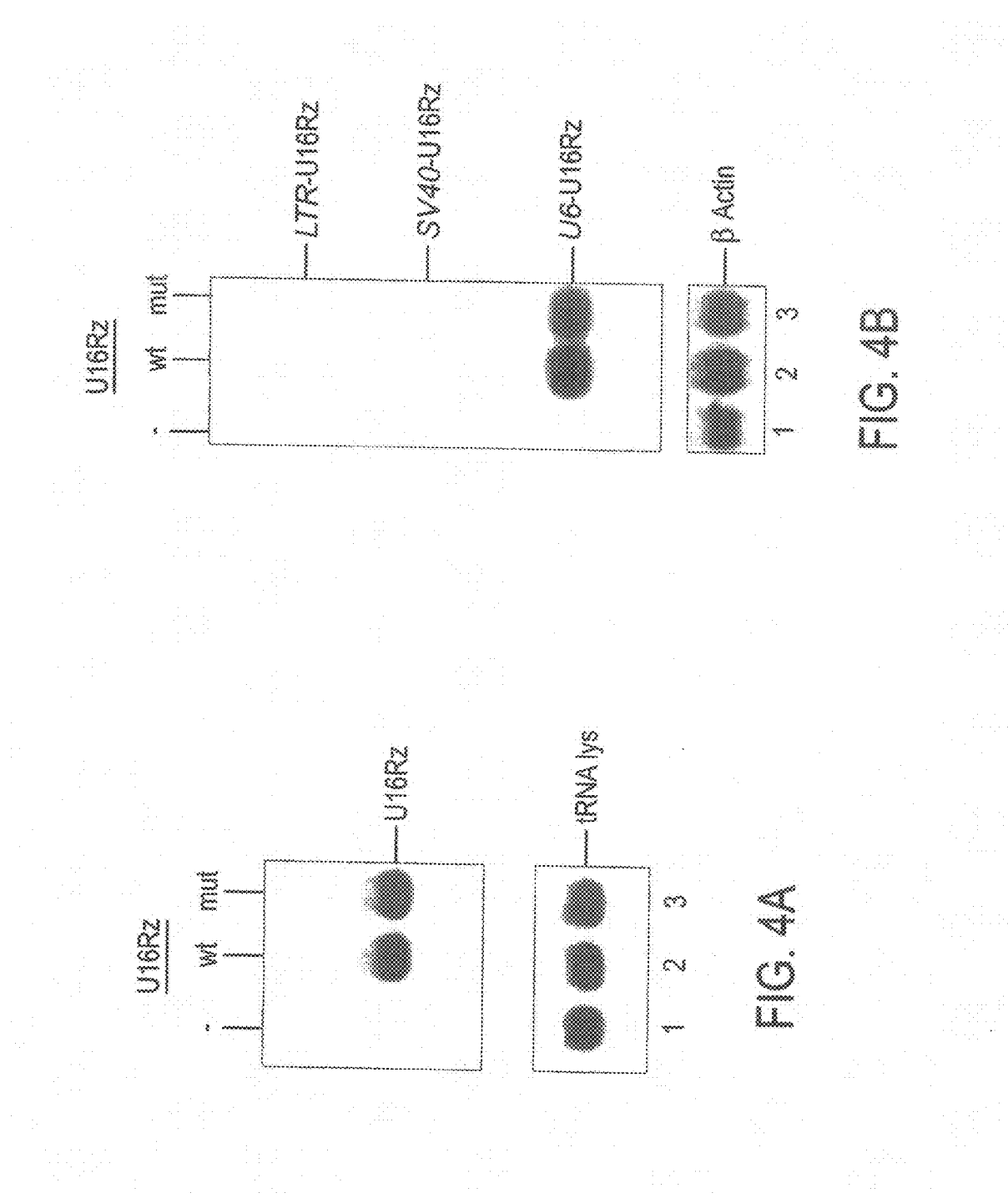

DUAL FILTER

FITC

DUAL FILTER

FITC

DUAL FILTER

FITC

DUAL FILTER

FITC

SEQUENCE LISTING

<160> NUMBER OF SEQ ID NOS: 12

<210> SEQ ID NO 1
<211> LENGTH: 52
<212> TYPE: DNA
<213> ORGANISM: synthetic construct

<400> SEQUENCE: 1
cttgcaatga tgtcgtaatt tgcgtcttac tctgttctca gcgacagttg aa        52

<210> SEQ ID NO 2
<211> LENGTH: 59
<212> TYPE: DNA

<213> ORGANISM: synthetic construct

<400> SEQUENCE: 2
tgtgcccgtt tcgtcctcac ggactcatca stgttgtgtg attttcaact gtcgctgag    59

<210> SEQ ID NO 3
<211> LENGTH: 52
<212> TYPE: DNA
<213> ORGANISM: synthetic construct

<400> SEQUENCE: 3
ggacgaaacg ggcacacaaa acctgctgtc agtaagctgg tacagaaggt tg    52

<210> SEQ ID NO 4
<211> LENGTH: 50
<212> TYPE: DNA
<213> ORGANISM: synthetic construct

<400> SEQUENCE: 4
tttcttgctc agtaagaatt ttcgtcaacc ttctgtacca gcttactgac    50

<210> SEQ ID NO 5
<211> LENGTH: 29
<212> TYPE: DNA
<213> ORGANISM: synthetic construct

<400> SEQUENCE: 5
cccccgagct ccttgcaatg atgtcgtaa    29

<210> SEQ ID NO 6
<211> LENGTH: 30
<212> TYPE: DNA
<213> ORGANISM: synthetic construct

<400> SEQUENCE: 6 cccccccaagc tttttcttgc tcagtaagaa    30

<210> SEQ ID NO 7
<211> LENGTH: 36
<212> TYPE: DNA
<213> ORGANISM: synthetic construct

<400> SEQUENCE: 7
ccccccccgt cgaccttgca atgatgtcgt aatttg    36

<210> SEQ ID NO 8
<211> LENGTH: 36
<212> TYPE: DNA
<213> ORGANISM: synthetic construct

<400> SEQUENCE: 8 ccctctaga aaaatttct tgctcagtaa gaattt    36

<210> SEQ ID NO 9
<211> LENGTH: 53
<212> TYPE: DNA
<213> ORGANISM: synthetic construct
<220> FEATURE:
<221> NAME/KEY: modified_base
<222> LOCATION: (2)..(2)
<223> OTHER INFORMATION: Aminoallyl T.
<220> FEATURE:
<221> NAME/KEY: modified_base
<222> LOCATION: (13)..(13)
<223> OTHER INFORMATION: Aminoallyl T.
<220> FEATURE:

```
<221> NAME/KEY: modified_base
<222> LOCATION: (24)..(24)
<223> OTHER INFORMATION: Aminoallyl T.
<220> FEATURE:
<221> NAME/KEY: modified_base
<222> LOCATION: (41)..(41)
<223> OTHER INFORMATION: Aminoallyl T.
<220> FEATURE:
<221> NAME/KEY: modified_base
<222> LOCATION: (52)..(52)
<223> OTHER INFORMATION: Aminoallyl T.

<400> SEQUENCE: 9
gntctctccc tcncactccc caanacggag agaagaacga ncatcaatgg cng            53

<210> SEQ ID NO 10
<211> LENGTH: 56
<212> TYPE: DNA
<213> ORGANISM: synthetic construct
<220> FEATURE:
<221> NAME/KEY: modified_base
<222> LOCATION: (1)..(1)
<223> OTHER INFORMATION: Aminoallyl T.
<220> FEATURE:
<221> NAME/KEY: modified_base
<222> LOCATION: (14)..(14)
<223> OTHER INFORMATION: Aminoallyl T.
<220> FEATURE:
<221> NAME/KEY: modified_base
<222> LOCATION: (30)..(30)
<223> OTHER INFORMATION: Aminoallyl T.
<220> FEATURE:
<221> NAME/KEY: modified_base
<222> LOCATION: (42)..(42)
<223> OTHER INFORMATION: Aminoallyl T.
<220> FEATURE:
<221> NAME/KEY: modified_base
<222> LOCATION: (55)..(55)
<223> OTHER INFORMATION: Aminoallyl T.

<400> SEQUENCE: 10
ntttgtgtgc ccgnttcgtc ctcacggacn catcagtgtt gngtgatttt caacng         56

<210> SEQ ID NO 11
<211> LENGTH: 50
<212> TYPE: RNA
<213> ORGANISM: synthetic construct
<220> FEATURE:
<221> NAME/KEY: misc_feature
<222> LOCATION: (15)..(15)
<223> OTHER INFORMATION: This is a C for wild-type and G for the mutant.

<400> SEQUENCE: 11
aaaaucacac aacasugaug aguccgugag gacgaaacgg gcacacaaaa                50

<210> SEQ ID NO 12
<211> LENGTH: 27
<212> TYPE: RNA
<213> ORGANISM: synthetic construct
<220> FEATURE:
<221> NAME/KEY: misc_feature
<222> LOCATION: (13)..(13)
<223> OTHER INFORMATION: This is C for the wild-type and G for the
      mutant.

<400> SEQUENCE: 12
ccagaucuga gcsugggagc ucucugg                                         27
```

NUCLEOLAR TARGETING OF THERAPEUTICS AGAINST HIV

CROSS-REFERENCE TO RELATED APPLICATIONS

This application is a continuation of U.S. Ser. No. 10/902,145, filed Jul. 30, 2004 (now abandoned), which is a divisional of U.S. Ser. No. 09/864,873, filed May 25, 2001, now U.S. Pat. No. 6,995,258, which claims the benefit of U.S. Ser. No. 60/206,976, filed May 25, 2000, each of which is incorporated by reference in their entirety.

STATEMENT REGARDING FEDERALLY SPONSORED RESEARCH

This work was supported by PHS grants AI29329 and AI42552. The federal government may have certain rights in this invention.

BACKGROUND OF THE INVENTION

AIDS (acquired immunodeficiency syndrome) is a deadly disease caused by the human immunodeficiency virus (HIV) which is a retrovirus. Despite intense research for nearly twenty years, a cure for AIDS has not yet been developed. Present treatments increase the life expectancy of AIDS patients, but extremely high mortality rates continue.

The expression of human immunodeficiency virus type 1 (HIV-1) is controlled by a post-transcriptional mechanism. From a single primary transcript several mRNAs are generated. These RNAs can be divided into three main classes: unspliced 9-kb, singly spliced 4-kb and the multiply spliced 2-kb RNAs. Each of these RNAs is exported to the cytoplasm for translation and, in the case of the 9 kb RNA, for packaging into virions (Kingsman and Kingsman, 1996; the publications and other materials used herein to illuminate the background of the invention or provide additional details respecting the practice, are incorporated by reference, and for convenience are respectively grouped in the appended List of References). Normally, pre-mRNAs must undergo a splicing process to remove one or more introns before being exported to the cytoplasm. HIV overcomes this limitation, allowing singly spliced and unspliced RNA to be exported via interaction with its own encoded Rev protein. Rev is responsible for the expression and cytoplasmic accumulation of the singly spliced and unspliced viral mRNAs by direct interaction with a target sequence (Rev response element or RRE) present in these mRNAs. This regulatory protein binds an RNA stem-loop structure (the RRE) located within the env coding region of singly spliced and unspliced HIV RNAs (Zapp and Green, 1989; Cochrane et al., 1990; D'Agostino et al., 1995; Malim et al., 1990). Binding of Rev to this element promotes the export, stability and translation of these HIV-1 RNAs (Arrigo and Chen, 1991; D'Agostino et al., 1992; Emerman et al., 1989; Feinberg et al., 1986; Felber et al., 1989; Hammarskjold et al., 1989; Lawrence et al., 1991; Schwartz et al., 1992; Malim et al., 1989; Favaro et al., 1999; Hope, 1999). The export process is mediated by the nuclear export signal (NES) of Rev which is a leucine rich region which binds the receptor exportin 1/CRM1 which mediates the export of the viral RNA. It is believed that CRM1 bridges the interaction of Rev with the nucleoporins required for export to the cytoplasm (Hope, 1999).

When Rev and Tat are expressed independently of other HIV transcripts, these proteins localize within the nucleolus of human cells (Cullen et al., 1988; Luznik et al., 1995; Dundr et al., 1995; Endo et al., 1989; Siomi et al., 1990; Stauber and Pavlakis, 1998). The simultaneous presence of a nuclear export signal (NES) as well as a nuclear import/localization signal (NLS) confers upon Rev the ability to shuttle between the nucleus and the cytoplasm (Hope, 1999). The Rev protein preferentially accumulates in the nucleolus in Rev-expressing cells (in the absence of RRE-containing RNA) and in the early phase of HIV infection (Dundr et al., 1995; Luznik et al., 1995). The reason for this specific sub-cellular localization is unknown. One possibility is that the nucleolus functions as the storage site for the Rev protein. Another and more compelling alternative, is that the Rev protein moves from the nucleus to the cytoplasm through the nucleolus. There is evidence that in the nucleolus Rev recruits nucleoporins Nup 98 and Nup 214 via hCRM1 (Zolotukhin and Felber, 1999). These results suggest a Rev-hCRM1-nucleoporins committed or pre-committed cytoplasmic export complex assembles in the nucleolus, and that the nucleolus can play a critical role in the Rev function.

To date, published data concerning nucleolar localization of HIV-1 RNAs are inconclusive. Using electron microscopy and in situ hybridization, Romanov et al. (1997) detected a subgenomic mRNA expressing the HIV-1p37gag (containing the RRE element) in all the subcellular compartments (including the nucleoli) of HL Tat cells. Interestingly, they observed that the expression of Rev induced relocalization of HW RNAs into two nonrandom patterns. One of these, the long track in the nucleoplasm, was radially organized around and in contact with the nucleoli. Other investigators using in situ hybridization analyses performed on mammalian cell lines transfected with different HIV-1 subgenomic or genomic constructs failed to detect HIV-1 RNA in the nucleolus (Zhang et al., 1996; Boe et al., 1998; Favaro et al., 1998; Favaro et al., 1999). The discrepancy in these results might be due to the different HIV-1 constructs, cell lines, and in situ hybridization protocols used by the various investigators. Furthermore, it should be taken into consideration that RNA export is a dynamic process; the rate of export as well as the amount of the HIV-1 RNA passing through the nucleolus can be limiting factors for in situ hybridization-mediated detection of nucleolar localized transcripts.

Ribozymes are RNA molecules that behave as enzymes, severing other RNAs at specific sites into smaller pieces. The hammerhead ribozyme is the simplest in terms of size and structure and can readily be engineered to perform intermolecular cleavage on targeted RNA molecules. These properties make this ribozyme a useful tool for inactivating gene expression, ribozymes being very effective inhibitors of gene expression when they are colocalized with their target RNAs (Sullenger and Cech, 1993; Samarsky et al., 1999). They may be valuable therapeutic tools for repairing cellular RNAs transcribed from mutated genes or for destroying unwanted viral RNA transcripts in the cell. However, targeting ribozymes to the cellular compartment containing their target RNAs has proved a challenge. Now, Samarsky et al. (1999) report that a family of small RNAs in the nucleolus (snoRNAs) can readily transport ribozymes into this subcellular organelle.

Small nucleolar RNAs (snoRNAs) are small, stable RNAs that stably accumulate in the nucleolus of eukaryotic cells. There are two major classes of snoRNA, each with its own highly conserved sequence motif. Both classes are involved in the post-transcriptional modification of the ribosomal RNA. The C/D box snoRNAs regulate 2'-O-methylation of the ribose sugars of ribosomal RNAs (rRNAs), and the H/ACA box snoRNAs guide pseudouridylation of rRNA uridine bases. A few snoRNAs also participate in processing precursor rRNA transcripts (Lafontaine and Tollervey, 1998; Weinstein and Steitz, 1999; Pederson, 1998). Most snoRNAs are transcribed and processed in the nucleus, although some may be synthesized in the nucleolus (the nuclear site of rRNA synthesis). It has been reported that the C and D boxes are important for stability, processing and nucleolar localization. In particular it has been demonstrated that an artificial RNA bearing the two boxes can be delivered into the nucleolus.

Samarsky et al. chose yeast for their experiments because the requirements for trafficking of a specific snoRNA (called U3) are well understood in this organism. They showed that nucleolar localization of the yeast U3 snoRNA was primarily dependent on the presence of the C/D box motif (Samarsky et al., 1998). The investigators appended a test ribozyme to the 5' end of U3, and then inserted its RNA target sequence into the same location in a separate U3 construct. So both the ribozyme and its target were expressed in separate, modified U3 snoRNAs. The snoRNA-ribozyme molecule (called a snorbozyme) and its U3-tethered target were transported into the nucleolus. Here the ribozyme cleaved its target RNA with almost 100% efficiency.

Three crucial prerequisites for effective ribozyme action are (i) colocalization of the ribozyme and its RNA target in the same place, (ii) accessibility of the cleavage site in the target RNA to pairing with the ribozyme, and (iii) high levels of ribozyme relative to target RNA (Sullenger and Cech, 1993; Lee et al., 1999). The importance of colocalization was first demonstrated by tethering a ribozyme to the packaging signal (psi) of a murine retroviral vector and showing that copackaging of the ribozyme with a psi-tethered target resulted in greater than 90% reduction in viral infectivity (Sullenger and Cech, 1993).

Samarsky and colleagues used a clever method to assay ribozyme activity based on the rate of appearance of one of the two cleavage products (see the figure in Rossi, 1999a). The RNA target tethered to U3 is stable, with a half-life of over 90 minutes, and its cleavage by the ribozyme generates two products: a short, rapidly degraded 5' fragment and a 5' extended form of the U3 snoRNA. The 5' extension itself gets degraded, leaving intact the U3 hairpin, which is quite stable and easily distinguished from endogenous U3. Taking advantage of the accumulation of this stable product, the investigators were able to measure the kinetics of ribozyme cleavage in vivo. By using similar assay systems, it is possible to analyze ribozyme cleavage kinetics for virtually any ribozyme-substrate combination under physiological conditions.

There are plenty of applications for snorbozymes, particularly as the nucleolus is proving to be more than just the place where rRNA is synthesized. For example, precursor transfer RNAs (Bertrand et al., 1998), RNA encoding the enzyme telomerase, signal recognition particle RNAs, and U6 snRNAs all pass through the nucleolus where they are either processed or receive base and/or backbone modifications (Weinstein and Steitz, 1999). Several RNAs have been reported to pass through the nucleolus for processing, particle assembly, or other modification (Pederson, 1998). These include c-myc, N-myc, and myoD1 mRNAs (Bond and Wold, 1993), the signal recognition particle RNA (Jacobson and Pederson, 1998; Politz et al., 2000), U6 small nuclear RNA (Tycowski et al., 1998), some pre-tRNAs in yeast (Bertrand et al., 1998), and the RNAse P RNA (Jacobson et al., 1997). There is also evidence that telomerase RNA is processed within the nucleolus (Mitchell et al., 1999; Narayanan et al., 1999b). Transcription and replication of the neurotropic Boma disease virus have also been shown to occur within the nucleolus (Pyper et al., 1998). Importantly, the HTLV-1 env RNAs have been demonstrated to be partially localized in the nucleolus (Kalland et al., 1991). HTLV-1 and HIV-1 have a similar posttranscriptional regulation mechanism, and the Rex protein, a functional homolog of HIV-1 Rev, also has nucleolar localization properties. Viral proteins such as HIV's Rev and Tat and HTLV-1's Rex accumulate in this subcellular organelle (Stauber and Pavlakis, 1998; Siomi et al., 1988; Cullen et al., 1988). Rev is a crucial regulatory protein that shuttles unspliced viral RNA from the nucleolus into the cytoplasm. Recent findings show that Rev itself is transported out of the nucleolus by binding to a Rev-binding element in a U16 snoRNA (Buonomo et al., 1999). Using a snoRNA to localize a ribozyme that targets viral RNA to the nucleolus may be an effective therapeutic strategy to combat HIV. Ribozymes, antisense RNAs, and RNA decoys that bind Rev or Tat may be more effective in the nucleolus than in other regions of the nucleus or cytoplasm. SnoRNA chimeras harboring ribozymes or protein-binding elements should prove valuable not only therapeutically but also for elucidating why certain RNAs and proteins traffic through the nucleolus.

SUMMARY OF THE INVENTION

The present invention extends the above prior knowledge by attaching an anti-HIV agent to a snoRNA to deliver the agent to the nucleolus where it will be in close contact with the virus and can inactivate the virus. The U3 snoRNA of yeast has been used as a vector to deliver a functionally active hammerhead ribozyme against a modified U3 snoRNA target in *Saccharomyces cerevisiae*. Disclosed herein, the human U16 snoRNA is used as a vector to deliver an anti-HIV-1 hammerhead ribozyme directed to a conserved sequence within the 5' LTR sequence of the HIV-1 RNA. The U16 snoRNA is also used as a vector to deliver a TAR element, which binds Tat, to the nucleolus. These chimeric RNAs are stably expressed in the nucleoli of human cells and single stable clones of the CEM T-lymphoblastoid cell lines expressing the ribozyme show a high degree of resistance to HIV-1 infection, whereas use of a disabled version of the ribozyme or TAR does not result in resistance to HIV-1 infection. High levels of infection of the stable clones expressing the wt as well as mutant version of the ribozyme were obtained using the HIV-2 strain (which does not contain the target sequence recognized by the ribozyme). These results prove the specific activity of the ribozyme and also show the activity of TAR to inhibit HIV replication. The nucleolar localized ribozymes elicit the greatest level of anti-HIV activity of any ribozymes we have tested.

One aspect of the invention is an RNA molecule comprising 1) a portion of a snoRNA and ii) an HIV TAR element.

A second aspect of the invention is a method for inhibiting HIV replication in a HIV infected cell comprising introducing a TAR element into said HIV infected cell.

A third aspect of the invention is an RNA molecule comprising i) a portion of a snoRNA and ii) a ribozyme.

A fourth aspect of the invention is a method for inhibiting HIV replication in a HIV infected cell comprising introducing a ribozyme into said HIV infected cell.

BRIEF DESCRIPTION OF THE FIGURES

The file of this patent contains at least one drawing executed in color. Copies of this patent with color drawings will be provided by the Patent and Trademark Office upon request and payment of the necessary fee.

FIGS. 4A-B show Northern blots of total RNA from HeLa CD4$^+$ cells transfected with the pBabe puro retroviral vector constructs. FIG. 4A shows results from RNA electrophoresed on a 6% polyacrylamide/7 M urea gel. FIG. 4B shows results from RNA electrophoresed on a 1% agarose/formaldehyde gel.

DETAILED DESCRIPTION OF THE INVENTION

Figures 1A, 1B:
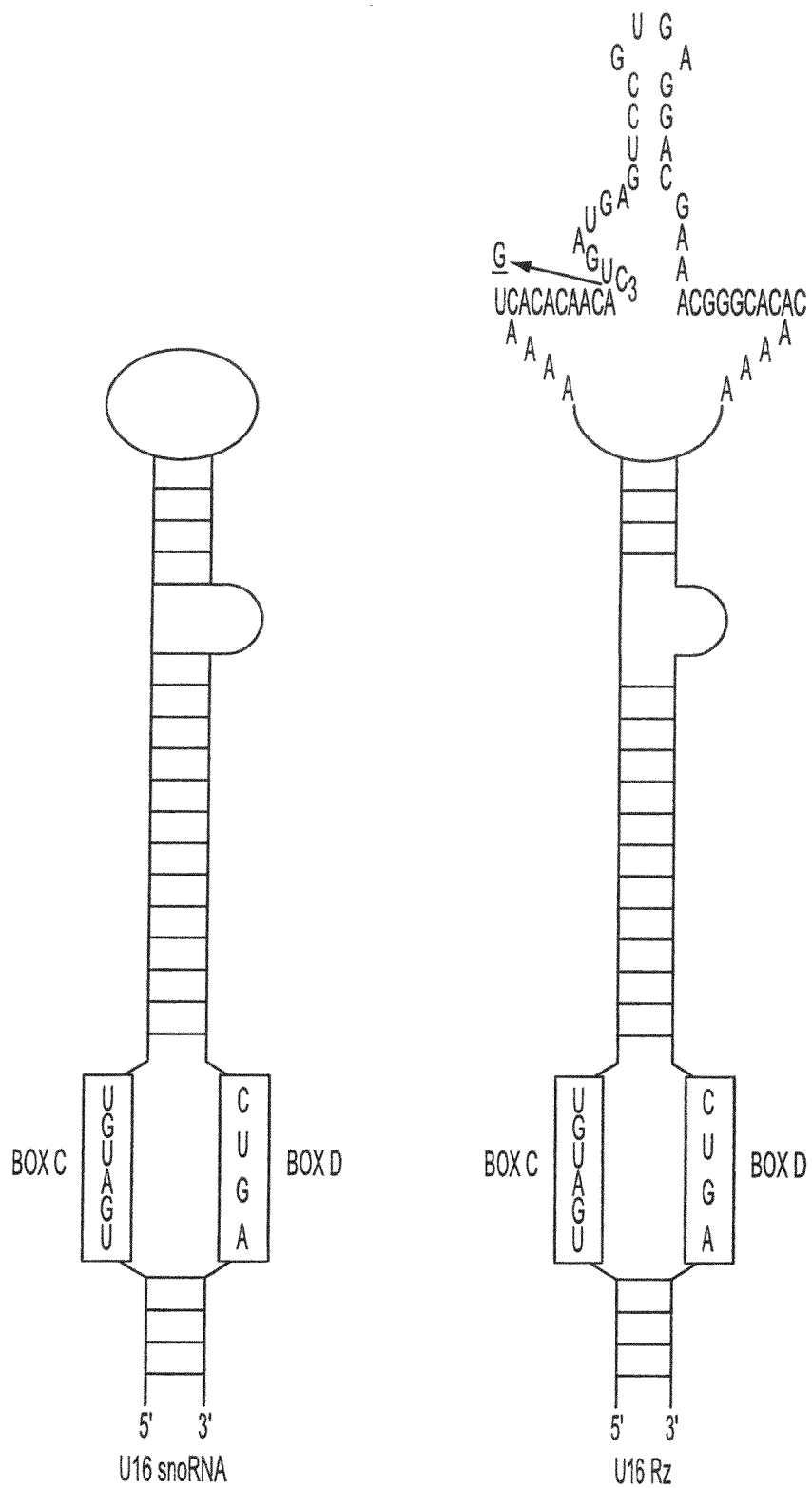
FIGS. 1A and 1B are schematic representations of U16 snoRNA and U16-hammerhead ribozyme (U16Rz), respectively. The sequence shown in FIG. 1B is SEQ ID NO:11.

There are two aspects to the invention. The first is the use of a human U16 snoRNA as a vector to deliver to a cell an anti-HIV-1 hammerhead ribozyme directed to a conserved sequence within the 5' LTR sequence of the HIV-1 RNA. The second aspect of the invention is the use of a human U16 snoRNA as a vector to deliver to a cell a TAR element which binds Tat.

I. Use of a Human U16 Snorna as a Vector to Deliver an Anti-HIV-1 Hammerhead Ribozyme We have taken advantage of the catalytic activity and nucleolar localization properties of a C/D box motif snoRNA fused to an anti-HIV-1 hammerhead ribozyme to address the question of whether HIV-1 RNAs pass through the nucleolus. To determine whether this trafficking takes place, a hammerhead ribozyme targeted to a highly conserved sequence in the U5 region of HIV-1 was delivered into the nucleoli of human cells. The ability of this nucleolar-localized ribozyme to inhibit the replication of HIV-1 was demonstrated in HeLa CD4$^+$ and CEM T lymphocytes, which are markedly resistant to HIV-1 infection as a consequence of ribozyme-mediated cleavage of HIV-1. These results can be best explained by nucleolar trafficking of HIV RNAs, making them susceptible targets for ribozyme-mediated inhibition. The inhibition of HIV by a nucleolar localized ribozyme has important implications for the biology and pathogenesis of HIV-1 infection, as well as therapeutic potential.

The nucleolus is known to serve primarily as the site of ribosome biogenesis, but recent findings have shown that this organelle is plurifunctional (Pederson, 1998), and numerous RNAs, including some messenger, small nuclear and viral RNAs transiently traffic through the nucleolus for covalent modification and functional associations with proteins (Rossi, 1999a).

It has been recently reported that in HeLa cells, the expression of Rev induces the re-localization of the nucleoporins Nup98 and Nup214, along with a significant fraction of CRM1, into the nucleolus (Zolotukhin and Felber, 1999). This result has led to the hypothesis that formation of the Rev-CRM1-nucleoporin complex targeted to the nuclear pore complex (NPC) occurs in the nucleolus. Thus, it can be similarly hypothesized that the unspliced and singly spliced HIV-1 RNAs, the Rev cognate binding substrates, are also re-localized to the nucleolus prior to cytoplasmic export.

Our approach for addressing the question of whether or not HIV-1 RNAs traffic through the nucleolus takes advantage of the catalytic activity and nucleolar localization properties of a C/D motif snoRNA fused to a hammerhead ribozyme, which specifically binds and cleaves a highly conserved sequence contained in the 5' LTR of HIV-1 RNA.

Ribozyme Construction

As a test of this hypothesis, we delivered a hammerhead ribozyme (Rossi, 1999b) targeted against a conserved sequence located in the 5' LTR of HIV-1 RNA into the nucleoli of human T-lymphoblastoid CEM cells and tested its ability to inhibit HIV-1 replication. We chose the well-studied U16 snoRNA (Fragapane et al., 1993) as the RNA vector for nucleolar localization of a hammerhead ribozyme targeted against a conserved sequence in the 5' LTR of HIV-1 RNA (Ojwang et al., 1992). U16 is a member of the C/D box class of small nucleolar RNAs (snoRNAs) (Weinstein and Steitz, 1999). Members of this class of snoRNAs primarily guide 2'-O-methylation of the ribose moiety of specific pre-rRNA nucleotides, although some members of this class are involved in pre-rRNA processing (Weinstein and Steitz, 1999). Moreover, Buonomo et al. (1999) have demonstrated that a chimeric U16 RNA harboring an HIV-1 Rev binding element (RBE) could be localized to the nucleolus following transcription from the human U6 small nuclear RNA promoter.

Since both Tat and Rev are RNA binding proteins, we hypothesized that they could traffic HIV RNAs into the nucleolus, where they would be susceptible to ribozyme mediated cleavage due to very discrete co-localization. To test this, we made a chimeric construct in which an anti-HIV ribozyme targeting a highly conserved site in the U5 region of the LTR was inserted in a non-essential region of the small nucleolar RNA (snoRNA) U16. To express the chimeric U16-ribozyme we utilized the U6+1 promoter, which is devoid of U6 snRNA sequences. The entire construct was inserted within the 3' LTR of the murine retroviral vector pBABE Puro, and constructs were stably transduced into CEM cells.

The apical loop of U16 snoRNA (FIG. 1A) was used to insert the anti-HIV-1 hammerhead ribozyme (U16Rz, FIG. 1B). U16 snoRNA is folded in a stem and loop structure, the C and D boxes are highlighted (FIGS. 1A-B). The C and D boxes are the nucleolar signal (Lange et al., 1998; Samarsky et al., 1998), in addition they are important for the stability and processing of U16 (Caffarelli et al., 1998). The U16 apical loop was chosen as a cloning site for a hammerhead ribozyme designed to cleave at position +115 relative to the transcription initiation site of the HIV-1 (U16Rz) (Ratner et al., 1985). A functionally disabled ribozyme was constructed by mutating the $C_3$ nucleotide of the hammerhead catalytic core to a G (FIG. 1B) (Hertel et al., 1992), and was used as a negative control in these studies. The chimeric U16Rz was shown to site-specifically cleave an HIV-1 transcript in vitro, whereas the disabled ribozyme had no cleavage activity.

Plasmid Constructs

The U16Rz was prepared synthetically by PCR (Dillon and Rosen, 1990) using the primers A, B, C, D, E and F.

A:
(SEQ ID NO: 1)
5'-CTTGCAATGATGTCGTAATTTGCGTCTTACTCTGTTCTCAGCGACAG

TTGAA-3'

B:
(SEQ ID NO: 2)
5'-TGTGCCCGTTTCGTCCTCACGGACTCATCA(C/G)TGTTGTGTGATT

TTCAACTGTCGCTGAG-3'

C:
(SEQ ID NO: 3)
5'-GGACGAAACGGGCACACAAAACCTGCTGTCAGTAAGCTGGTACAGAA

GGTTG-3'

D:
(SEQ ID NO: 4)
5'-TTTCTTGCTCAGTAAGAATTTTCGTCAACCTTCTGTACCAGCTTACT

GAC-3'

E:
(SEQ ID NO: 5)
5'-CCCCCGAGCTCCTTGCAATGATGTCGTAA-3'

F:
(SEQ ID NO: 6)
5'-CCCCCCAAGCTTTTTCTTGCTCAGTAAGAA-3'

The B primer contains an equimolar mixture of C and G nucleotides at the position indicated to simultaneously generate by PCR the wild-type (wt) and mutant versions of U16Rz. The PCR product was sub-cloned in the SacI and HindIII sites of the pGEM 9zf(-) vector (Promega), giving rise to the pGEM/U16Rz wt and mutant constructs. These constructs were linearized with HindIII and transcribed in vitro to test their catalytic activity against an RNA oligonucleotide containing the HIV-1 RNA target.

This target site is highly conserved among several HIV isolates and it has been already reported to be an accessible region in vitro and in vivo (Ojwang et al., 1992). The sequence of the hammerhead active core was derived from the studies of Uhlenbeck and Haseloff (Uhlenbeck, 1987; Haseloff and Gerlach, 1988; Ruffner et al., 1990). Four adenosines were added to each side of the hammerhead ribozyme in order to enlarge the loop of U16 and facilitate interaction of the ribozyme with the HIV-1 target site.

U16Rz wt and mutant sequences were cloned in the U6 snRNA expression cassette giving rise to the clones U6+1/U16Rz wt and U6+1/U16Rz mut. The U16Rz wt and mutant sequences were amplified by PCR from the pGEM/U16Rz wt and mutant constructs using the SalI 5' and XbaI 3' primers.

SalI 5':
(SEQ ID NO: 7)
5'-CCCCCCCCGTCGACCTTGCAATGATGTCGTAATTTG-3'

XbaI 3':
(SEQ ID NO: 8)
5'-CCCCTCTAGAAAAAATTTCTTGCTCAGTAAGAATTT-3'

The PCR products were ligated in the SalI and XbaI sites of the pTz/U6+1 expression cassette (Good et al., 1997) generating the U6+1/U16Rz wt and mutant constructs. The pTz/U6+1 cassette contains the U6 promoter that allows transcription driven by RNA pol III but does not contain the sequence elements necessary for 5' capping, which might interfere with the nucleolar localization encoded in the C/D motif of U16. Six thymidines were added at the 3' end of the ribozyme coding sequence to terminate RNA polymerase III transcription.

The BamHI-XbaI fragments from U6+1/U16Rz wt and mutant constructs (containing the U6 promoter) were filled in and the resulting fragment was inserted in both orientations in the NheI site of the pBabe puro retroviral vector (U3 region of the 3' long terminal repeat (LTR)), giving rise to the following constructs: pBabe Puro/U16Rz F (wt and mutant) and pBabe Puro/U16Rz R (wt and mutant).

Figure 2A:
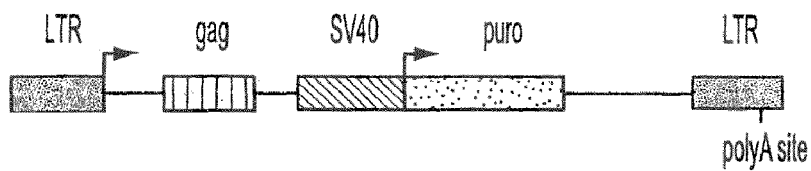
FIGS. 2A-C are schematics showing how U16Rz wt and mutant sequences were cloned in the U6 snRNA expression cassette giving rise to the clones U6+1/U16Rz wt and U6+1/U16Rz mut.
Figure 2B:
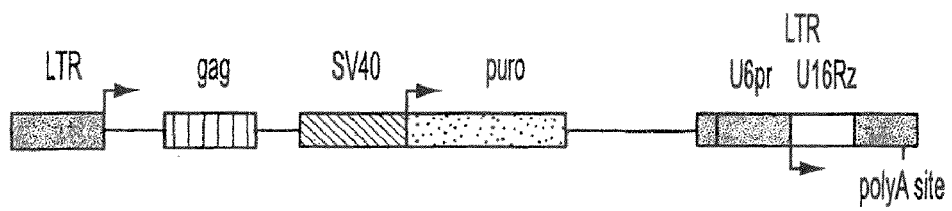
Figure 2C:
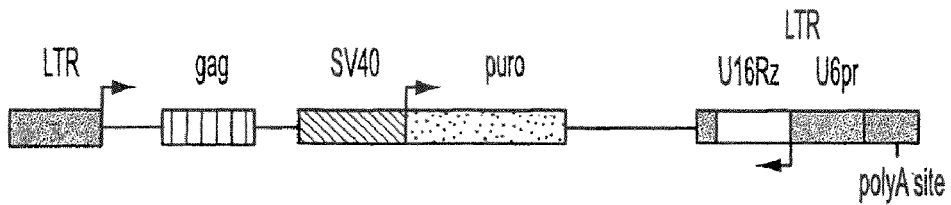

FIGS. 2A-C show a schematic representation of pBabe Puro retroviral constructs. FIG. 2A shows pBabe Puro parental vector (Morgenstern and Land, 1990). The expression cassette U6+1/U16Rz wt and U16Rz mutant were cloned in both orientations in the 3' LTR (U3 region) of the vector, giving rise to the constructs pBabe puro/U16Rz wt or U16Rz mutant, F (forward) and pBabe puro/U16Rz wt or U16 Rz mutant, R (reverse). FIG. 2B shows pBabe Puro/U16Rz wt or U16Rz mutant F: The U6 expression cassette is in the same transcriptional orientation as the 5' LTR and SV40 promoters contained in the pBabe vector. FIG. 2C shows pBabe Puro/U16Rz wt or U16Rz mutant R: The U6 expression cassette is in the opposite transcriptional direction with respect to the 5' LTR and SV40 promoters contained in the pBabe vector.

These constructs contain the U6 promoter that allows the transcription driven by the RNA pol III, but do not contain the sequence elements necessary for the 5' capping which might interfere with the nucleolar localization encoded in the C/D motif of U16. Six thymidines were added at the 3' end of the ribozyme coding sequence to terminate RNA pol III transcription.

Cell Culture 293 cells (American Type Culture Collection: CRL 1573) and HeLa-CD4-LTR-β-gal cells (obtained from the AIDS Research and Reference Reagent Program no. 1470) were both propagated in Dulbecco's modified Eagle's medium with high glucose (Irvine Scientific) supplemented with 10% FBS (GIBCO/BRL), 200 mM L-glutamine (Irvine Scientific), penicillin G (10 units/mL, GIBCO/BRL), streptomycin (10 mg/mL, GIBCO/BRL), and 0.2 mg/mL G418 (GIBCO/BRL) and 0.1 mg/mL hygromycin (H-Sigma) only for the HeLa-CD4-LTR-β-gal cells. Transfection and infection of the cells were carried out in the absence of any antibiotics. Cells were plated at approximately $1 \times 10^6$ cells per 100 mm dish, one day prior to the transfection. The cells where then transiently transfected with 2-10 μg of DNA, using a Calcium Phosphate Kit (Gibco-BRL). Forty-eight hours after transfection, HeLa-CD4-LTR-β-gal cells were selected in 1.5 μg/ml puromycin (Sigma) to obtain uniformly selected pools. CEM cells were maintained in RPMI medium 1640 supplemented with 10% FCS (Irvine Scientific), penicillin (10 units/mL; Irvine Scientific), and streptomycin (100 μg/mL; Irvine Scientific).

Packaging Cell Line

The Phoenix Packaging cell line (Nolan Lab at Stanford University ("standford.edu/group/nolan")) was cultured in Dulbecco's modified Eagle's medium (Irvine Scientific) containing 10% FCS (Irvine Scientific), penicillin (10 units/mL, Irvine Scientific) and streptomycin (100 µg/mL, Irvine Scientific) and plated at 1.5×10⁶ cells per 60 mm dish one day prior to transfection. Five minutes before the transfection 25 µM chloroquine was added to each plate. The cells where then transiently transfected with 6 µg of the different pBabe puro constructs (pBabe Puro/U16Rz R wt and mutant and pBabe Puro/U16Rz F wt and mutant) using a Calcium Phosphate Kit (Gibco-BRL). Eight hours after transfection the precipitate was washed and replaced by fresh media. 32 hours after transfection fresh media was exchanged for the spent media. 48 hours after transfection a pellet of 1×10⁶ CEM cells was resuspended with 2.8 mL of virus (Phoenix cell supernatants) and 28 µL of Protamine sulfate {400 g/mL) and spun for 90 minutes at 2500 rpm at 32° C. After the spin, the virally infected CEM cells were incubated for 150 minutes at 37° C. The supernatant was then removed and the CEM cells resuspended in 5 mL of RPMI-1640 supplemented with 10% FCS (Irvine Scientific), penicillin (10 units/mL, Irvine Scientific) and Streptomycin (100 µg/mL, Irvine Scientific) and incubated for 48 hours at 37° C. under 5% $CO_2$ (Scherr et al., 2000). For puromycin-resistance selection, 1.5 µg/ml puromycin was added to the medium, and cells were incubated in the presence of this drug for 3 weeks to obtain pooled, drug-resistant populations of cells. Single stable clones were obtained from the pools by limiting dilution.

HIV Infectious Assays

Twenty-four hours before infection of the cells with HIV-I-IIIB, 1×10⁵ HeLa-CD4-LTR-β-gal cells were plated in 3 mL of medium per well in a six-well plate. Cells were infected in triplicate with 5 µL of HIV-1-IIIB overnight in the presence of 4 µg/mL protamine sulfate (Elkins-Sinn, Cherry Hill, N.J.). The HIV-1-IIIB viral stock had been propagated on peripheral blood lymphocytes and was determined to contain 1×10⁴ TCID50/mL. After overnight incubation the cells were washed three times with Hanks' balanced salts solution and refed with medium. Aliquots of medium for HIV-1 p24 antigen analysis were collected when cells reached confluency, 72 hours after infection. p24 values were determined with the HIV-1 p24 antigen capture assay (Science Applications International Corp., Frederick, Md.) according to the manufacturer's instructions. CEM cells (2.5×10⁵) derived from stable clones were infected with HIV-$1_{NL4-3}$ at a multiplicity of infection (moi) of 0.0002 (low moi experiment) and 0.002 (high moi experiment). Infections were performed in duplicate. After infection, the cells were resuspended in 12 mL of complete medium, and p24 accumulation in the supernatant was monitored over time. The cells were split and refed twice a week. The p24 analyses were performed using the HIV-1 p24 antigen capture assay kit (Science Applications International Corp., Frederick, Md.). For the high moi experiment the p24 analyses were performed on days 7 and 11, after which the pathogenic effects of the virus on the control cells made p24 determinations irrelevant.

RNA Preparation and Northern Blot Analyses

Total RNA was prepared using the RNA-STAT 60 reagent (Tel-Test "B"; Tel-Test, Friendswood, Tex.) according to the manufacturer's protocol. The RNA was electrophoresed in a 1% agarose/formaldehyde gel or a 6% polyacrylamide/7 M urea gel and blotted onto a nylon filter. To simultaneously detect the U16Rz RNA and the endogenous U16 small nucleolar RNA (snoRNA), we used a radiolabeled probe complementary to the 3' end of U16. To detect only the U16Rz RNA we used a probe complementary to the hammerhead ribozyme sequence. To detect the loading controls, we used probes specific for β-actin mRNA and $tRNA_3^{Lys}$.

In Situ Hybridization

We performed in situ hybridizations as previously described ("singerlab.aecom.yu.edu/protocols"). 293 cells were grown on cover slips and transiently transfected with 2 µg of the U6+1/U16Rz wt and U16Rz mutant constructs. After 48 hours the cells were fixed in 4% para-formaldehyde and the in situ hybridization analysis was carried out. For probes we used the following aminoallyl-T-modified primers:

U3:
(SEQ ID NO: 9)
5-GT*TCTCTCCCTCT*CACTCCCCAAT*ACGGAGAGAAGAACGAT*CAT

CAATGGCT*G-3'

U16Rz:
(SEQ ID NO: 10)
5'-T*TTTGTGTGCCCGT*TTCGTCCTCACGGACT*CATCAGTGTTGT*G

TGATTTTCAACT*G-3'

The T* indicates the aminoallyl-T nucleotides. The specific primer for U3 was chemically conjugated with the Cy3 fluorophore (CyTM3 monofunctional reactive dye; Amersham Pharmacia). The U16Rz probe was chemically conjugated with Oregon green 488 (Molecular Probes). Digital image processing was used to analyze the localization of U16Rz and U3 snoRNA within the 293 cells. Images were collected with an Olympus BX50 microscope (FIGS. 3A-D) and a DEI-50 video camera (Optronics). A 60× objective and FITC and Cy3 filters were used to detect the U16Rz and U3 snoRNA signals, respectively. A dual filter for FITC+Cy3 was also used to show the yellow overlapping signals from the two RNAs. A 4',6-diamidino-2-phenylindole (DAPI) filter was used to identify the nucleus (blue signal). The images in FIGS. 3E-G were collected with a Zeiss LSM310 laser scanning microscope at 6,400-fold magnification. HIV indirect immunofluorescence assays were performed as described previously (Sandstrom et al., 1985) on CEM-derived clones infected with HIV-$1_{NL4-3}$ or HIV-$2_{ROD}$. The images were collected with an Olympus BX50 microscope and a DEI-50 video camera (Optronics) with a 40× objective.

In Vivo Expression and Intracellular Localization of the U16Rz

Figure 3A:
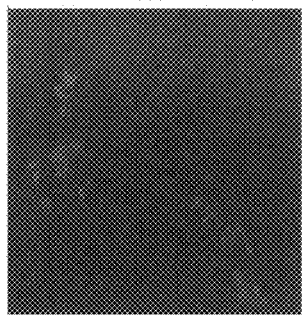
FIGS. 3A-D show in situ hybridization analyses of 293 cells transfected with 2 μg of the U6+1/U16 Rz wt and U16 Rz mutant constructs.
Figure 3B:
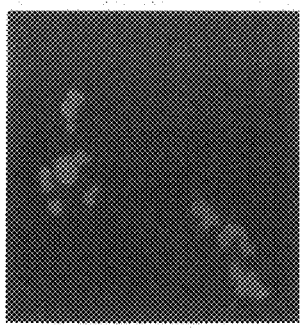
Figure 3C:
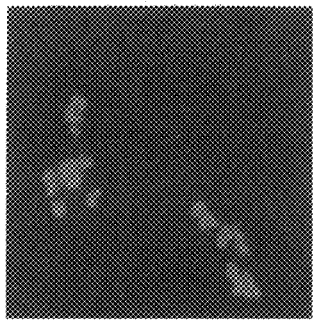
Figure 3D:
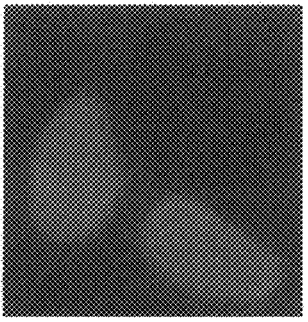
Figure 3G:
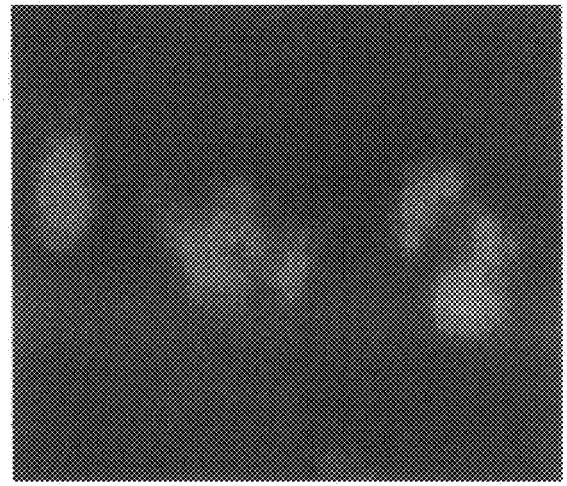
FIGS. 3E-G show a high-resolution confocal microscope analysis of the U3 snoRNA and U16Rz distribution in the nucleoli of transiently infected 293 cells.
Figure 3F:
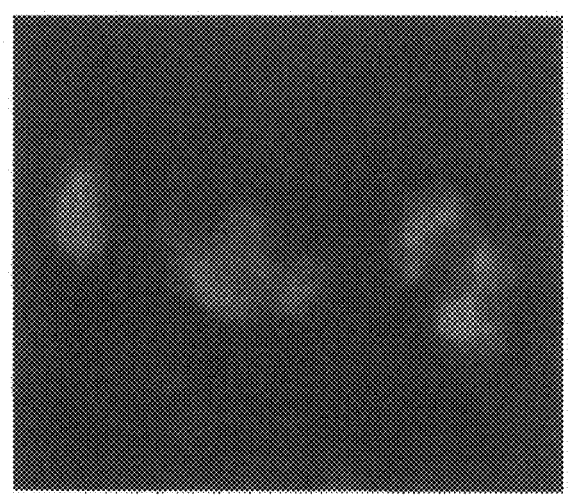
Figure 3E:

The chimeric U16/ribozyme RNAs were expressed by the human U6 small nuclear RNA promoter (clone U6+1) (Good et al., 1997) after transient transfection into human 293 cells, and in situ hybridization was carried out, using fluorescent probes to detect the U16Rz. A separate fluorescent probe was used to identify endogenous U3 snoRNA, which served as a nucleolar control. The pattern obtained demonstrated that the ribozyme and the U3 snoRNAs colocalize within the nucleoli (FIGS. 3A-G). Specifically, 293 cells were grown on coverslips and transiently transfected with 2 µg of the U6+1/U16Rz wt and U16Rz mutant constructs. After 48 hours the cells were fixed in 4% paraformaldehyde and the in situ hybridization was performed. FIG. 3A shows hybridization with the Oregon green 488 probe specific for the U16Rz. FIG. 3B shows hybridization with the Cy3 red probe specific for the U3 snoRNA, used to detect the nucleoli. FIG. 3C shows the overlap between the red signal of U3 and the green signal of U16Rz which appears as a yellow signal. FIG. 3D shows 4',6-diamidino-2-phenylindole staining to delineate the nuclei. Laser scanning confocal microscopy reveals partial overlap between the U3 snoRNA (red signal) and U16Rz (green signal) fluorescent signals within the nucleoli (FIGS. 3E-G). Some of the observed localization of U3 and the U16Rz may be in coiled bodies as well as the nucleoli, inasmuch as the studies of Narayanan et al. (1999a) suggest that coiled bodies can play a role in the biogenesis and/or intranuclear transport of the C/D box snoRNAs.

U16Rz in Vivo Activity

To test the effect of nucleolar localization of an anti-HIV-1 hammerhead ribozyme on HIV-1 infectivity, the chimeric U16Rz wt and the U16Rz mutant expression cassettes were inserted within the 3' LTR (U3 region) of the pBabe puro retroviral vector (Morgenstern and Land, 1990) in both orientations (forward (F) and reverse (R) with respect to the direction of transcription from the 5' LTR; FIGS. 2B-C). As a rapid preliminary test for efficacy of the U16Rz, HeLa CD4$^+$ cells were transfected with the different retroviral constructs, and pooled populations were selected for puromycin resistance. RNAs were isolated from these cells and analyzed for ribozyme expression (FIGS. 4A-B). Cells transfected with the pBabe/U16Rz clone in the F orientation expressed the highest levels of ribozymes. The Reverse orientation had several-fold lower expression. The reason for this difference is not known. We therefore utilized only the F orientation for subsequent analyses. Northern analyses demonstrate that the U16Rz is transcribed almost exclusively from the U6 small nuclear RNA promoter (FIG. 4B).

We assayed by HIV-1 infectious challenge the ribozyme-inhibitory effect of the pooled population of HeLa CD4$^+$ cells expressing the U16Rz wt and U16Rz mutant. HeLa CD4$^+$ cells were transfected with the pBabe puro retroviral vector constructs, and pooled populations were selected for puromycin resistance. Five micrograms of total RNAs was extracted from the different transfected HeLa CD4$^+$ pooled populations and electrophoresed in a 6% polyacrylamide/7 M urea gel (FIG. 4A) or in a 1% agarose/formaldehyde gel (FIG. 4B), blotted onto nylon filters, and hybridized with specific probes. To simultaneously detect the U16Rz RNA and the endogenous U16 small nucleolar RNA (snoRNA), we used a radiolabeled probe complementary to the 3' end of U16. To detect only the U16Rz RNA we used a probe complementary to the hammerhead ribozyme sequence. To detect the loading controls, we used probes specific for β-actin mRNA and tRNA$_3^{Lys}$. In FIGS. 4A and 4B, lane 1 contains total RNA extracted from parental HeLa CD4$^+$ cells. Lanes 2 and 3 contain total RNA extracted from the HeLa CD4$^+$ pooled populations transfected with either the pBabe puro/U16Rz wt or pBabe puro/U16Rz mutant, respectively, both in the F orientation.

Figure 5:
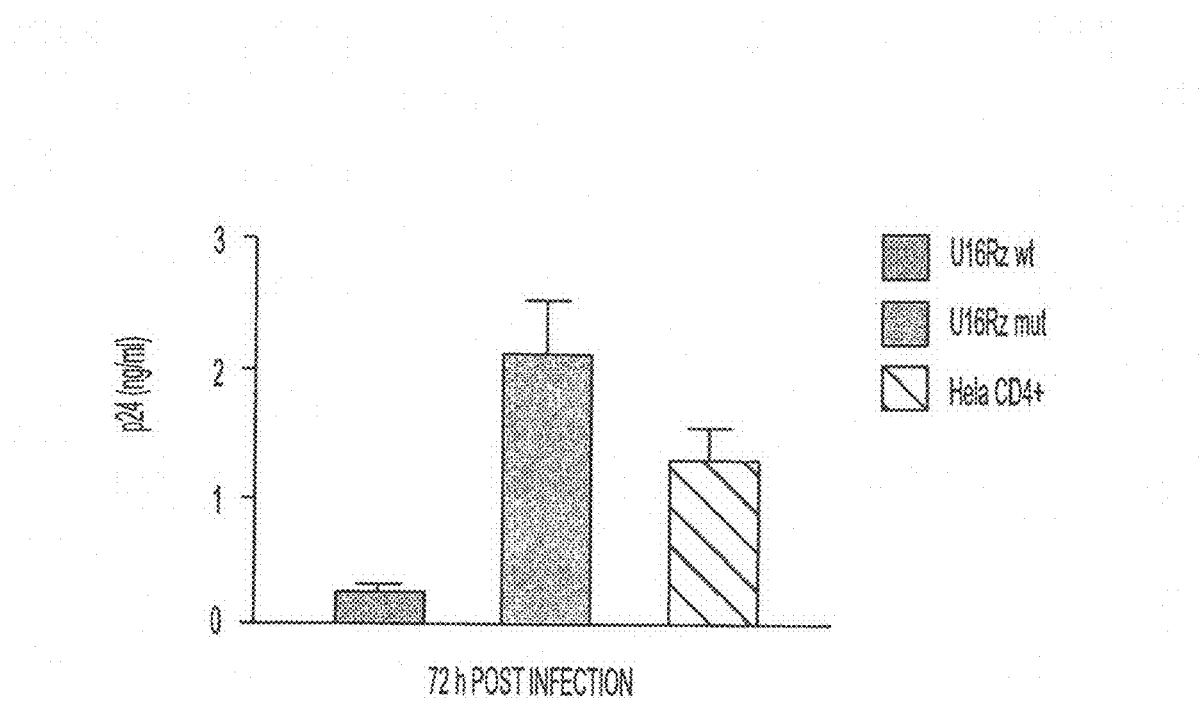
FIG. 5 shows HIV-1 p24 antigen accumulation 72 hours postinfection from pooled populations of HeLa CD4$^+$ cells expressing U16Rz wt, U16Rz mutant, or the untransfected parental HeLa CD4$^+$ cells infected with HIV-1-IIIB at an moi of 0.001.

The pooled populations of HeLa CD4$^+$ expressing U16Rz wt, U16Rz mutant, or the untransfected parental HeLa CD4$^+$ cells were infected with HIV-1-IIIB at an moi of 0.001. The HIV-1 p24 antigen accumulation was determined at 72 hours after infection. The data presented represent average values of four independent experiments, including the standard deviation. These results are shown in FIG. 5. The results of HIV-1 p24 analyses demonstrate that the nucleolar U16Rz wt confers protection from infection, whereas both the pooled populations expressing the U16Rz mutant and the parental HeLa CD4$^+$ cells are readily infectable by HIV-1 (FIG. 5).

Figures 6A, 6B:
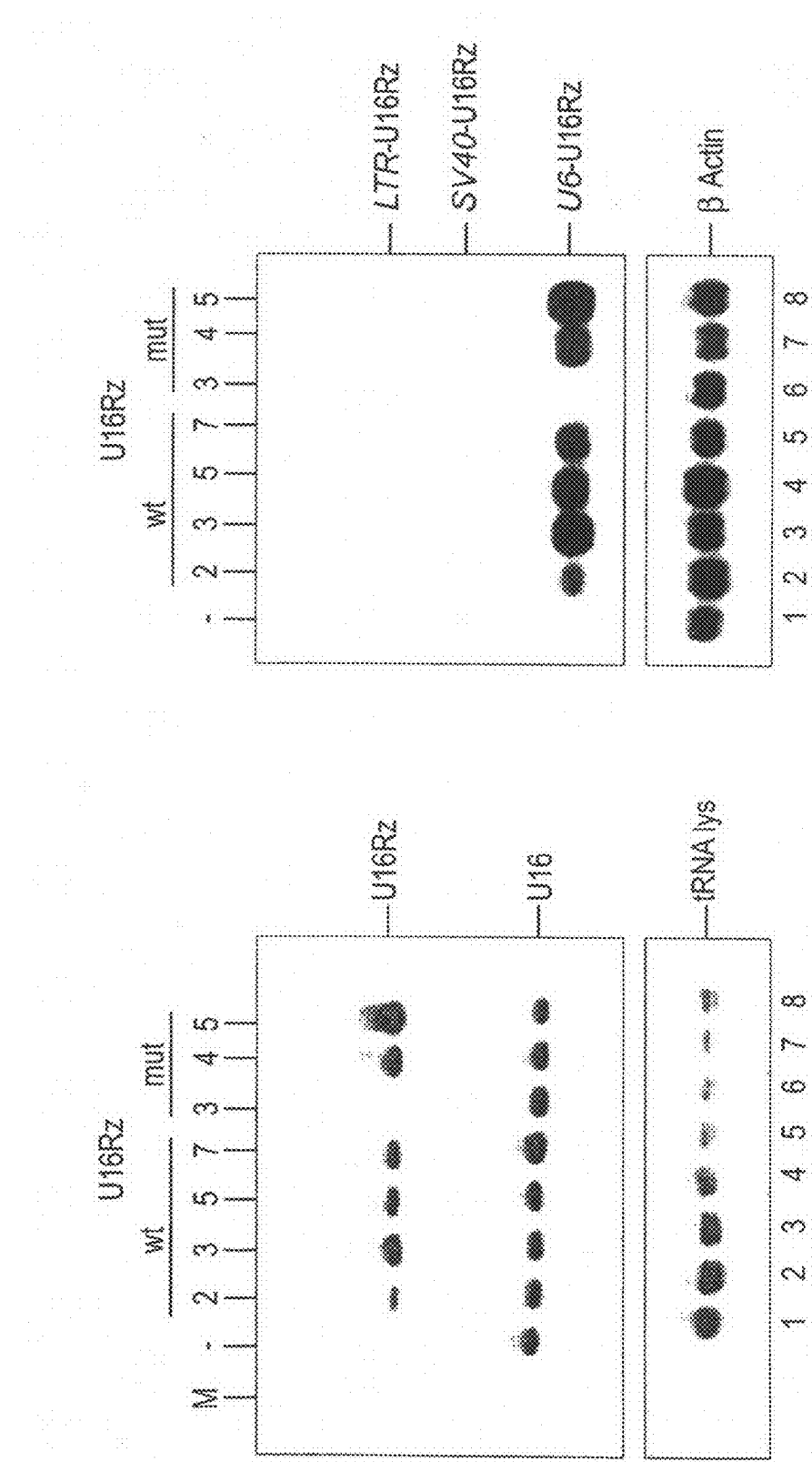
FIGS. 6A-B Northern blots from RNA run on a denaturing polyacrylamide gel (6A) or agarose-formaldehyde gel (6B). RNA was extracted from CEM cells transduced with different pBabe puro retroviral constructs.

To confirm the inhibitory effect of the U16Rz in a T cell model, the CEM T lymphoblastoid cell line was transduced with the same retroviral constructs (FIGS. 2A-C). Single stable clones were selected from the pooled population of puromycin-resistant cells, and the steady-state accumulation of ribozyme transcripts was analyzed by Northern blotting and hybridization (FIGS. 6A-B).

Human T lymphoblastoid CEM cells were transduced with the different pBabe puro retroviral constructs, and pooled populations were selected for puromycin resistance. Single stable clones were selected by limiting dilution from the pooled clones. Total RNAs (5 μg) from the single stable clones were electrophoresed in a denaturing polyacrylamide (FIG. 6A) or on an agarose-formaldehyde gel (FIG. 6B), blotted onto nylon filters, and hybridized with the specific probes as described above. Lane M contains the labeled HpaII-digested Bluescript KS (+) DNA used as a size marker. Lane 1 contains total RNA extracted from untransduced CEM cells. Lanes 2-5 contain total RNA extracted from single CEM stable clones 2, 3, 5, and 7, which were cloned from the CEM cell pool transduced with the pBabe puro/U16Rz wt, in the F orientation. Lanes 6-8 contain total RNA extracted from single CEM stable clones 3, 4, and 5 cloned from the CEM cell pool transduced with the pBabe puro/U16Rz mutant, in the F orientation. A low level of expression from the U16Rz mutant clone 3 can be observed after prolonged exposure of the hybridized blot.

In situ hybridization analysis performed on the stably transduced CEM cells confirmed the colocalization between U3 snoRNA and U16Rz. Three different single, stably transduced CEM clones expressing the U16Rz wt (2, 3, and 7) and two different clones expressing the U16Rz mutant (4 and 5) along with the untransduced parental CEM cells were used in HIV-1 challenge assays (FIGS. 6A-B). 1×10$^5$ cells were infected with HIV-1$_{NL4-3}$ at an moi of 0.0002. Infections were performed in triplicate. After infection, the cells were resuspended in 12 mL of complete media and p24 accumulation in the supernatant was monitored over time. The p24 analyses were performed using the HIV-1 p24 antigen capture assay kit (SAIC Frederick, Frederick, Md.). The HIV-1-encoded p24 accumulation was determined at days 7, 11, 17, and 25 after infection.

Figure 7:
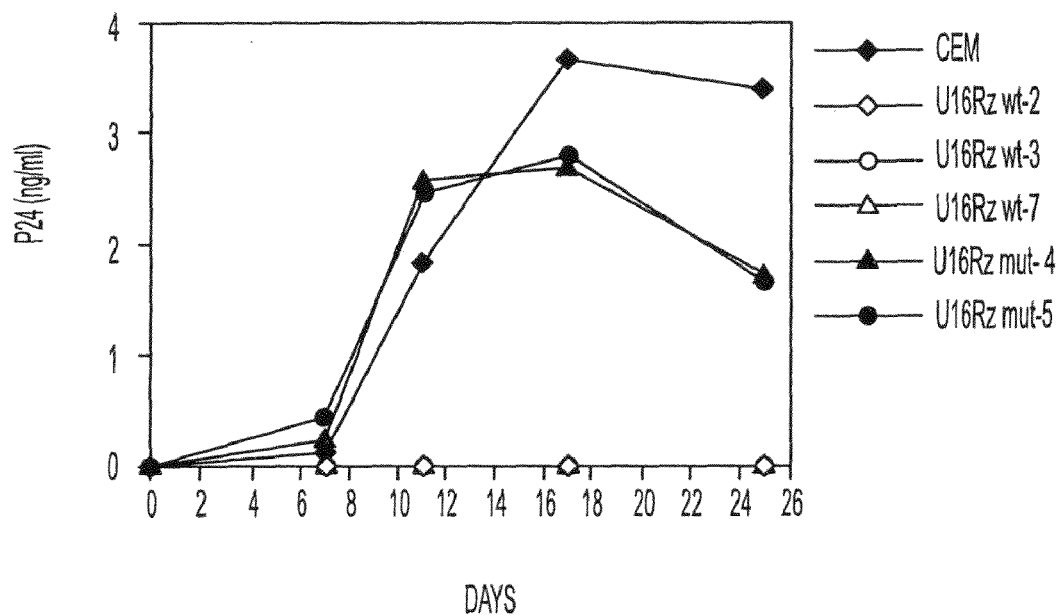
FIG. 7 shows HIV-1-encoded p24 accumulation in transduced CEM clones at days postinfection.
Figure 8A:
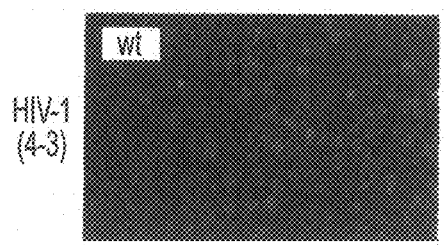
FIGS. 8A-H show HIV indirect immunofluorescence assays performed on infected CEM clones.
Figure 8B:
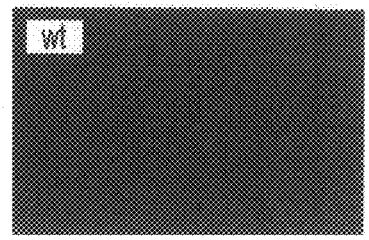
Figure 8C:
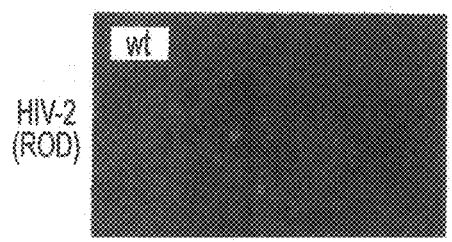
Figure 8D:
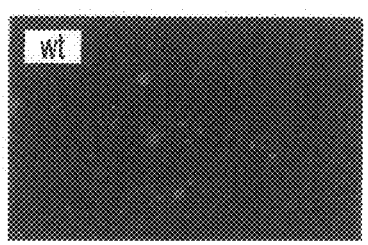
Figure 8E:
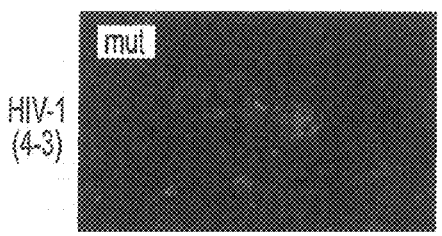
Figure 8F:
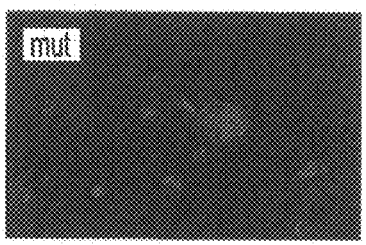
Figure 8G:
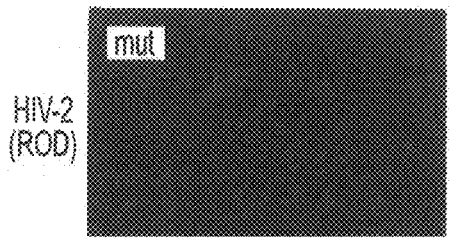
Figure 8H:
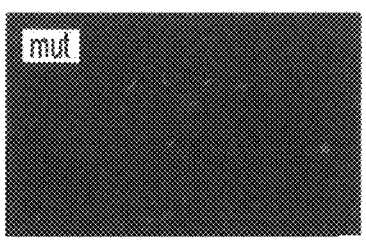
Figure 9A:
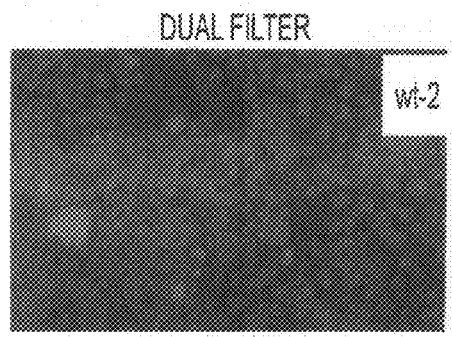
FIGS. 9A-L show HIV indirect immunofluorescence assays performed on infected CEM cells.
Figure 9B:
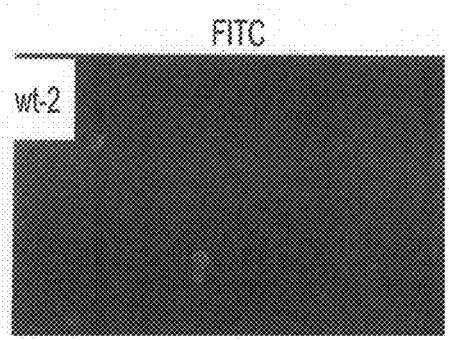
Figure 9C:
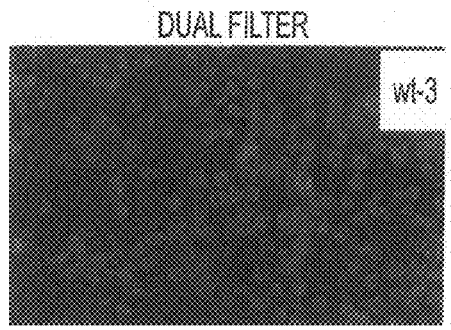
Figure 9D:
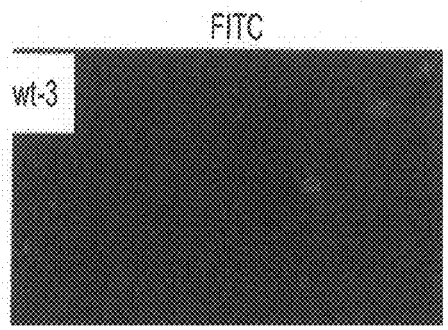
Figure 9E:
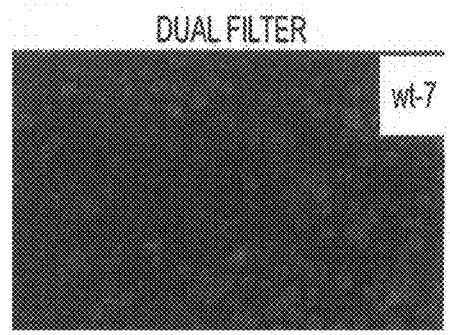
Figure 9F:
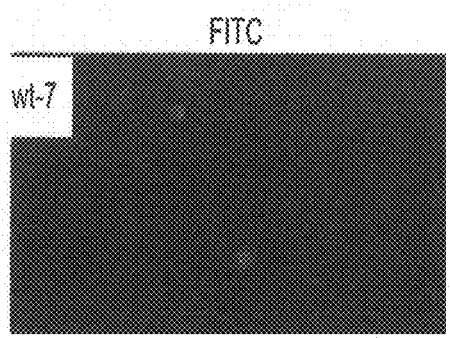
Figures 9G, 9H:
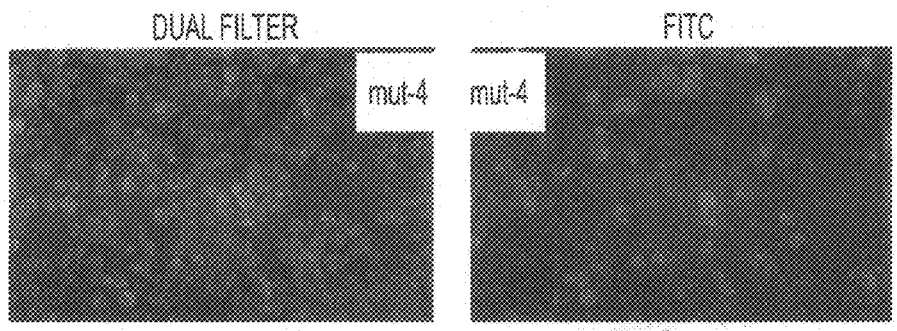
Figures 9I, 9J:
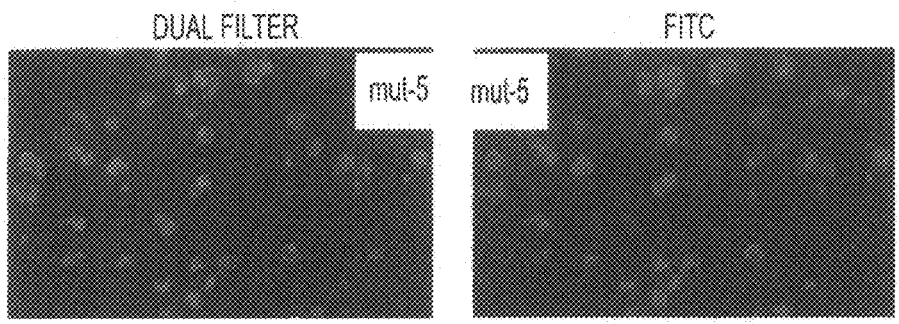
Figures 9K, 9L:
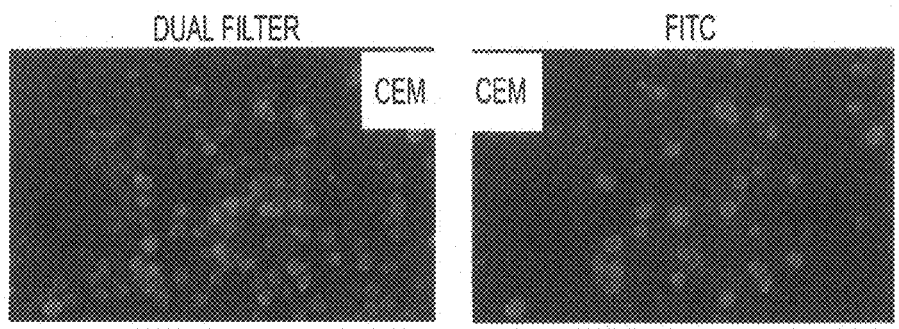
Figure 10:
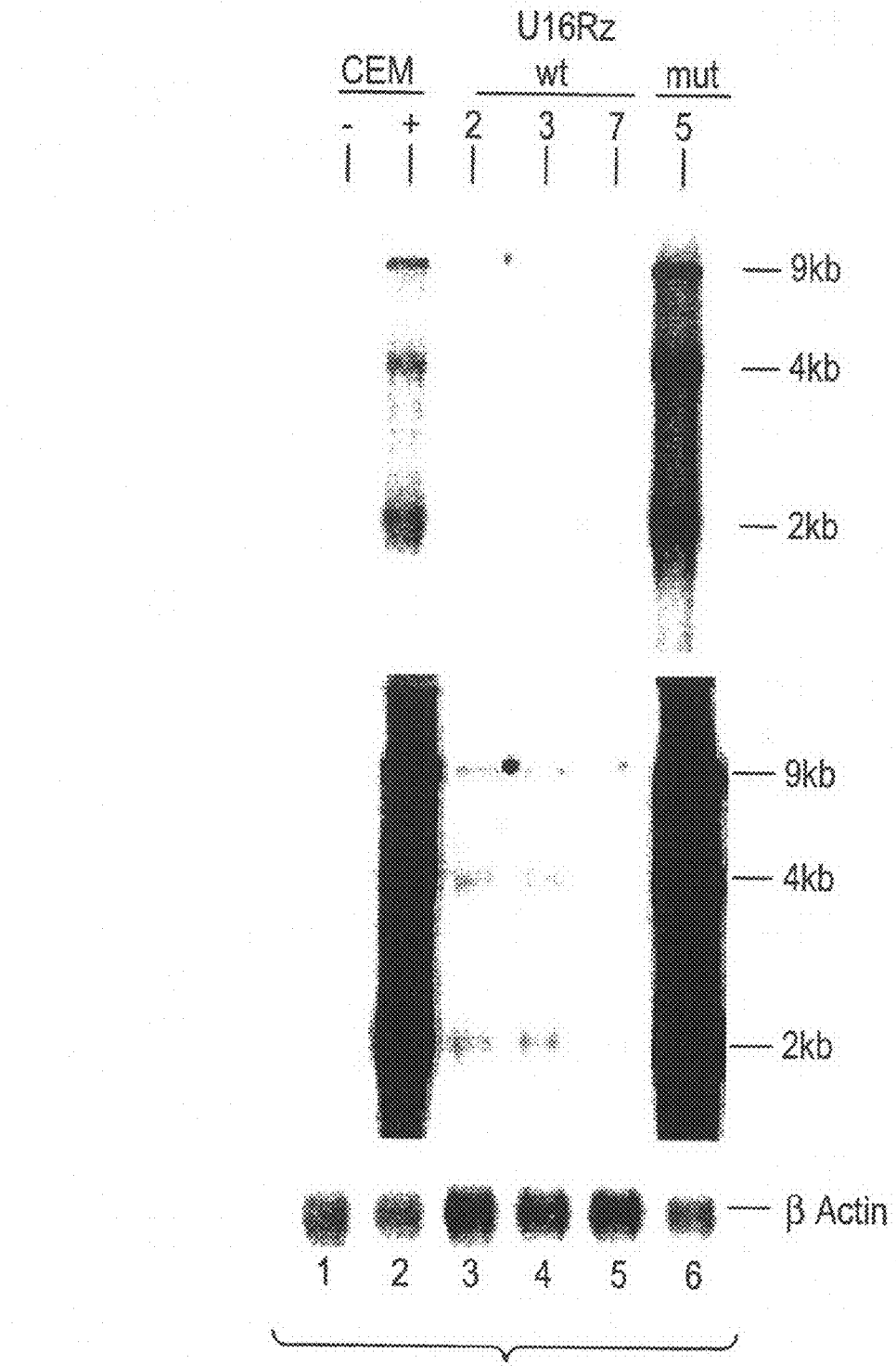
FIG. 10 shows a Northern blot analysis of RNA from HIV-1 infected CEM stable clones.

The results from these viral challenges showed no measurable HIV-1 p24 in the supernatants of the U16Rz wt clones during the 25-day period of analysis, whereas the untransduced CEM cells and U16Rz mutant clones gave rise to nanogram levels of p24 antigen (FIG. 7). The results of the p24 analysis were confirmed by an HIV indirect immunofluorescence assay using serum from an HIV-1-infected patient (FIGS. 8A-H). FIGS. 8A-H show HIV indirect immunofluorescence assays performed, as described previously (Sandstrom et al., 1985), using heat-inactivated HIV-1 seropositive human serum, on CEM clones expressing the U16Rz wt (clone 3) (FIGS. 8A-D) and U16Rz mutant (clone 4) (FIGS. 8E-H) infected with HIV-1$_{NL4-3}$ or HIV-2$_{ROD}$, at days 17 and 7 after infection, respectively. The infected cells are FITC-stained and fluoresce green. The cells were counterstained in 1% trypan blue dye in PBS. The images in FIGS. 8A, 8C, 8E and 8G were obtained with a dual filter (FITC/rhodamine). The uninfected cells appear red under the rhodamine filter, and infected cells exhibit a green fluorescence. The images in FIGS. 8B, 8D, 8F and 8H were acquired with just the FITC filter, revealing only the green fluorescence of the infected cells.

No HIV antigen staining was detected in the CEM stable clones expressing the U16Rz wt, whereas intense staining was detected in the U16Rz mutant clones, indicating viral production and spread in these cell cultures. The levels of CD4 expression for all of the cell lines used in the challenge assays were monitored, and no differences were observed.

To verify that the ribozyme-expressing CEM cells were resistant to HIV-1 as a consequence of ribozyme function, we challenged the U16Rz wt, U16Rz mutant, and untransduced CEM cells with HIV-2, which is CD4-tropic but does not harbor the ribozyme target site. All of the cell lines tested were readily infected by HIV-2, as shown by HIV-2 reverse transcriptase analyses and HIV indirect immunofluorescence analyses (FIGS. 8A-H). We next evaluated the extent of ribozyme-mediated inhibition of HIV-1 in the stably transduced CEM cell lines by using a 10-fold higher moi. Despite the higher moi used in this challenge, CEM clones expressing the U16Rz wt still showed a dramatic resistance to HIV-1 infection as monitored by HIV immunostaining and HIV-1 RNA levels (FIGS. 9A-L and 10).

HIV indirect immunofluorescence assays were performed as described for FIGS. 8A-H. The results are shown in FIGS. 9A-L. CEM clones 2, 3, and 7 expressing the U16Rz wt, clones 4 and 5 expressing the U16Rz mutant, and parental CEM cells were infected with HIV-1NL4-3 at an moi of 0.002. Immunofluorescence monitoring of infection was performed at day 11 after infection. The infected cells are FITC-stained (FIGS. 9B, 9D, 9F, 9H, 9J and 9L). The dual filter (FIGS. 9A, 9C, 9E, 9G, 9I and 9K) (FITC/rhodamine) shows uninfected cells (red) and infected cells (green).

Northern blot analysis (FIG. 10) was performed on 5-μg RNA samples electrophoresed in a 1% agarose/formaldehyde gel. Total RNAs were extracted from the above HIV-1-infected CEM stable clones. Hybridization was carried out with a Rev cDNA sequence. The signals obtained from the endogenous β-actin were used as loading controls. After overnight exposure (upper portion of FIG. 10) the HIV-1 RNA was detected only in the parental CEM cells (lane 2) and in the CEM clone 5 expressing the U16Rz mutant (lane 6). RNA prepared from uninfected CEM cells (lane 1) was used as a negative control. HIV-1 RNAs from the U16Rz wt-expressing clones 2, 3, and 7 (lanes 3, 4, and 5, respectively) was detectable only after 3 days of prolonged exposure of the hybridized filter, as shown in the middle portion of FIG. 10.

Measurements of p24 antigen demonstrated that some U16Rz wt-expressing cells had in fact been infected at this higher moi, but the immunofluorescence staining revealed that the extent of viral spread was dramatically reduced in comparison to the U16Rz mutant and CEM cell controls (FIGS. 9A-L).

Figures 11A, 11B:
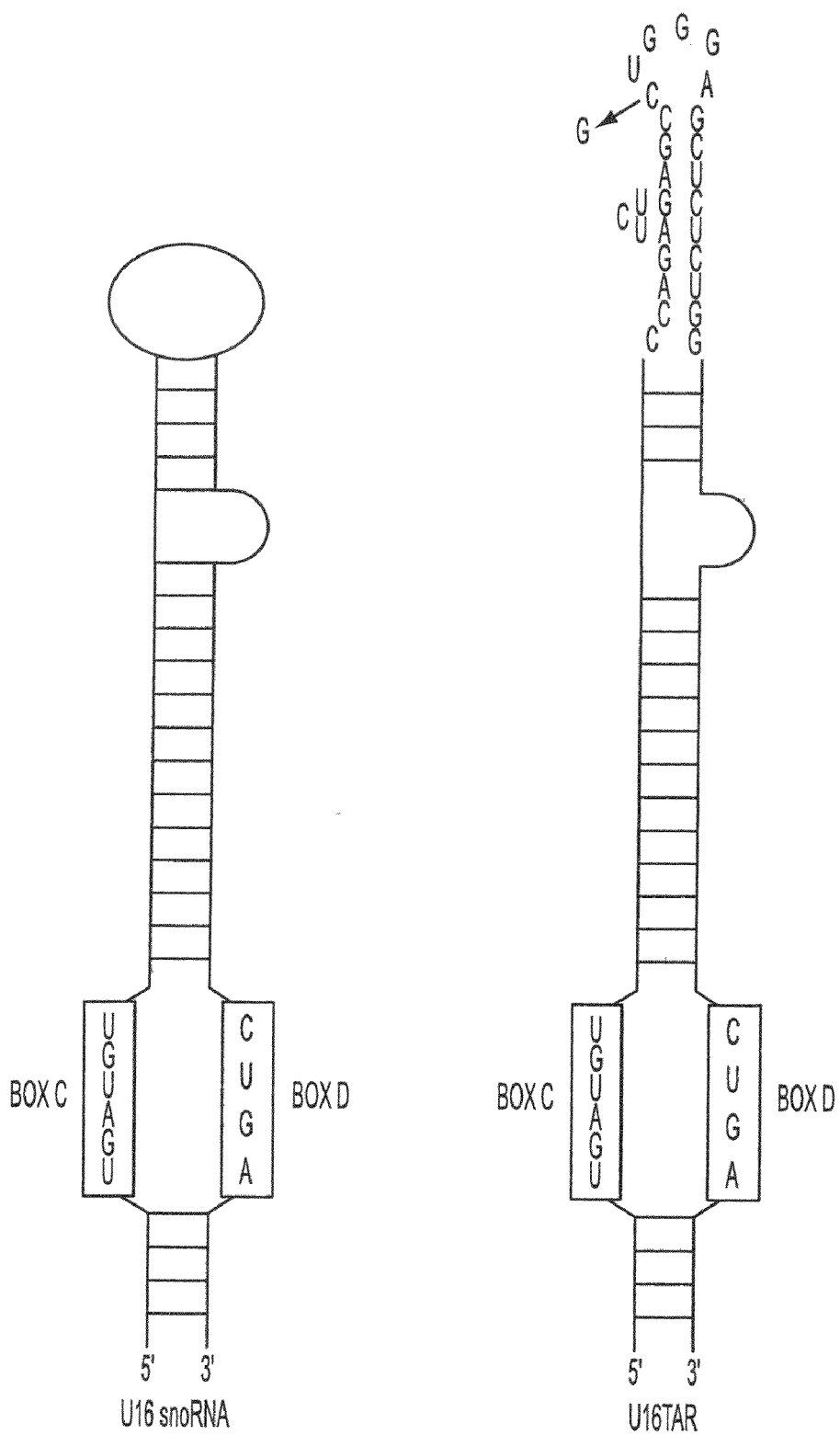
FIGS. 11A-B show schematic representations of U16 snoRNA (FIG. 11A) and U16TAR (FIG. 11B). The sequence shown in FIG. 11B is SEQ ID NO:12.

II. Use of a Human U16 snoRNA as a Vector to Deliver an Anti-HIV-IIIB TAR Element Use of a chimeric nucleolar Rev decoy to inhibit HIV replication has been reported (Michienzi et al., 1999). In that work a chimeric vector comprising U16 snoRNA and a Rev Binding Element (RBE) was constructed and was found to inhibit HIV replication. It is thought that the construct targets the nucleolus where it binds Rev thereby preventing Rev from acting to export viral RNA to the cytoplasm. To further examine the nucleolar localization properties of HIV regulatory proteins Tat and Rev, we have constructed a U16TAR-1 fusion construct (FIGS. 11A-B).

The Tat protein stimulates in trans the expression of all HIV-1 genes by several orders of magnitude (Feng and Holland, 1988). Cells infected with HIV-1 require tat protein to produce virus, suggesting that trans-activation is crucial for viral replication (Fisher et al., 1986; Dayton et al., 1986). The essential cis-acting site for trans-activation, termed tar, resides within the R region of the HIV-1 long terminal repeat (LTR), between −17 and +54 with respect to the initiation site of viral transcription (Rosen et al., 1985; Muesing et al., 1987).

TAR encodes an RNA step-loop structure which acts as a binding site for the Tat protein (Dingwall et al., 1989). There is a direct correlation between Tat binding to TAR RNA and trans-activation (Gait and Karn, 1993). In addition to acting as a binding site for Tat protein, the apical portion of TAR RNA also acts as a binding site for cellular RNA-binding proteins that participate in trans-activation (Sheline et al., 1991; Wu et al., 1991). DNA control elements essential for transcription initiation may also overlap TAR (Ratnasabapathy et al., 1990; Garcia et al., 1987; Zenzie-Gregory et al., 1993).

Figure 12:
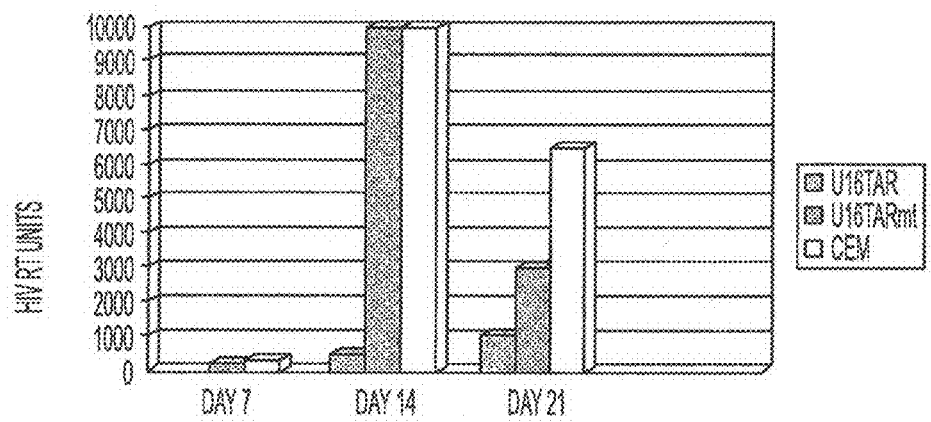
FIG. 12 shows the results of reverse transcriptase assays on pools of stably transduced CEM clones challenged with HIV-IIIB using a TCID50 of 50.

The chimeric RNA we have made is driven by the U6 promoter, and the transcriptional unit has been inserted within the 3' LTR of the pBabe puro retroviral vector. FIGS. 11A-B show the secondary structures of U16 snoRNA and chimeric U16TAR element. In addition to the wild-type TAR element, we have created a mutation in TAR-1 that reduces Tat binding fourfold (Sullenger et al., 1991). Both the wild type and mutant constructs have been stably transduced into CEM cells and challenged with HIV-IIIB. Only the wild type construct provided inhibition of this acute challenge. The results are shown in FIG. 12.

Stably transduced CEM cells expressing U16TAR, U16TAR mutant, or untransduced CEM were challenged with infectious HIVIIIB. A mutant version of the TAR element in which the indicated C to G transversion (Sullenger et al., 1991) which binds Tat with a four fold lower efficiency was made to create a negative control. The wild type and mutant TAR constructs were inserted downstream of the U6+1 promoter, and this transcriptional unit was cloned within the 3' LTR of the pBabe puro retroviral vector. The constructs were stably transduced into CEM cells. Expression of the constructs was monitored via Northern gel analyses and was robust. The pools of clones were challenged with HIV-IIIB using a TCID50 of 50. Reverse transcriptase assays were carried out and the average of quadruplicate RT measurements for 7, 14 and 21 days post infection (with backgrounds subtracted) plotted (see FIG. 12).

We have demonstrated that nucleolar localized ribozymes targeted to a sequence within the 5' LTR of HIV-1 RNA are able to dramatically inhibit replication of this virus. A chimeric U16 snoRNA plus TAR element also results in inhibition of HIV. These data provide an indirect demonstration that HIV-1 RNA, probably the unspliced 9 Kb and singly spliced 4 Kb transcripts harboring the RRE, pass through the nucleolus prior to cytoplasmic export. It is premature to assign a functional role for HIV-1 nucleolar trafficking or to conclude that all or a subset of HIV-1 transcripts participate in nucleolar trafficking. Importantly, the potent ribozyme-mediated inhibition of HIV-1 replication and inhibition by the U16TAR chimeric construct in our studies clearly demonstrates that a critical step in viral maturation is blocked by this approach. The results presented here, taken together with strong evidence from others for nucleolar localization of Rev and Tat, indicate that HIV-1 RNA is processed through the nucleolus in the later stages of the replicative cycle. The marked inhibitory activity of our U16Rz and U16TAR constructs against HIV-1 infection makes these prime candidates for anti-HIV-1 therapy. This fact is true regardless of whether the chimeric constructs act within the nucleolus as hypothesized or whether they act elsewhere and we are not bound by the theory that the action occurs in the nucleolus.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Arrigo S J and Chen I S Y (1991). *Genes Dev.* 5:808-819.
Bertrand E, et al. (1998). *Genes Dev.* 12:2463-2468.

Boe S-O, et al. (1998). *Virology* 244:473-482.
Bond V C and Wold B (1993). *Mol. Cell. Biol.* 13:3221-3230.
Buonomo S B, et al. (1999). *RNA* 5:993-1002.
Caffarelli E, et al. (1998). *Mol. Cell Biol.* 18:1023-1028.
Cochrane A W, et al. (1990a). *Proc. Natl. Acad. Sci.* 87:1198-1202.
Cullen B R, et al. (1988). *J. Virol.* 62:2498-2501.
D'Agostino D M, et al. (1992). *Mol. Cell. Biol.* 12:1375-1386.
D'Agostino D M, et al. (1995). *AIDS Res. Hum. Retroviruses* 11:1063-1071.
Dayton A I, et al. (1986). *Cell* 44:941-947.
Dillon P J and Rosen C A (1990). *BioTechniques* 9:298-300.
Dingwall C, et al. (1989). *Proc. Natl. Acad. Sci. U.S.A.* 86:6925-6929.
Dundr M, et al. (1995). *J. Cell Sci.* 108:2811-2823.
Emerman M, et al. (1989). *Cell* 57:1155-1165.
Endo S, et al. (1989). *Virus Genes* 3:99-110.
Favaro J P, et al. (1998). *Virology* 249:286-296.
Favaro J P, et al. (1999). *Virology* 255:237-249.
Feinberg M B, et al. (1986). *Cell* 46:807-817.
Felber B K, et al. (1989). *Proc. Natl. Acad. Sci.* 86:1495-1499.
Feng S and Holland E C (1988). *Nature (London)* 334:165-168.
Fisher A G, et al. (1986). *Nature (London)* 320:367-371.
Fragapane P, et al. (1993). *EMBO J.* 12:2921-2928.
Gait M J and Karn J (1993). *Trends Biochem. Sci.* 18:255-259.
Garcia J A, et al. (1987). *EMBO J.* 6:3761-3770.
Good P D, et al. (1997). *Gene Ther.* 4:45-54.
Hammarskjold M L, et al. (1989). *J Virol.* 63:1959-1966.
Haseloff J and Gerlach W L (1988). *Nature (London)* 334:585-591.
Hertel K J, et al. (1992). *Nucleic Acids Res.* 20:3252.
Hope T J (1999). *Archives of Biochemistry and Biophysics* 365:186-191.
Jacobson M R and Pederson T (1998). *Proc. Natl. Acad. Sci. U.S.A.* 95:7981-7986.
Jacobson M R, et al. (1997). *J. Cell Sci.* 110:829-837.
Kalland K-H, et al. (1991). *New Biol.* 3:389-397.
Kingsman S M and Kingsman A J (1996). *Eur. J. Biochem.* 240:491-507.
Lafontaine D L and Tollervey D (1998). *Trends Biochem. Sci.* 23:383-388.
Lange T S, et al. (1998). *EMBO J.* 17:3176-3187.
Lawrence J B, et al. (1991). *New Biol.* 3:1220-1232.
Lee N S, et al. (1999). *RNA* 5:1200-1209.
Luznik L, et al. (1995). *AIDS Res. and Hum. Retroviruses* 11:795-804.
Malim M H, et al. (1989). *Nature (London)* 338:254-257.
Malim M H, et al. (1990). *Cell* 60:675-683.
Michienzi A L, et al. (1999). *The Nucleic Acids Symposium Series* 41:211-214.
Michienzi A, et al. (2000). *Proc. Natl. Acad. Sci. U.S.A.* 97:8955-8960.
Mitchell J R, et al. (1999). *Mol. Cell Biol.* 19:567-576.
Morgenstern J P and Land H (1990). *Nucleic Acids Res.* 18:3587-3596.
Muesing M A, et al. (1987). *Cell* 48:691-701.
Narayanan A, et al. (1999a). *Mol. Biol. Cell* 10:2131-2147.
Narayanan A, et al. (1999b). *EMBO J.* 18:5120-5130.
Ojwang J O, et al. (1992). *Proc. Natl. Acad. Sci. U.S.A.* 89:10802-10806.
Pal B K, et al. (1998). *J. Virol.* 72:8349-8353.
Pederson T (1998). *Nucleic Acids Res.* 26:3871-3876.
Politz J C, et al. (2000). *Proc. Natl. Acad. Sci. U.S.A.* 97:55-60.
Pyper J M, et al. (1998). *J. Virol.* 72:7697-7702.
Ratnasabapathy R, et al. (1990). *Genes Dev.* 4:2061-2074.
Ratner L, et al. (1985). *Nature (London)* 313:277-284.
Romanov V I, et al. (1997). *Virology* 228:360-370.
Rosen C A, et al. (1985). *Cell* 41:813-823.
Rossi J J (1999a). *Science* 285:1685.
Rossi J J (1999b). *Chem. Biol.* 6:R33-37.
Ruffner D E, et al. (1990). *Biochemistry* 29:10695-10702.
Samarsky D A, et al. (1998). *EMBO J.* 17:3747-3757.
Samarsky D A, et al. (1999). *Proc. Natl. Acad. Sci. U.S.A.* 96:6609-6614.
Sandstrom E G, et al. (1985). *Transfusion* 25:308-312.
Scherr M, et al. (2000). *Mol. Ther.* 2:26-38.
Schwartz S, et al. (1992). *J. Virol.* 66:150-159.
Sheline C T, et al. (1991). *Genes Dev.* 5:2508-2520.
Siomi H, et al. (1988). *Cell* 55:197-209.
Siomi H, et al. (1990). *J. Virol.* 64:1803-1807.
Stauber R H and Pavlakis G N (1998). *Virology* 252:126-136.
Sullenger B A, et al. (1991). *J. Virol.* 65:6811-6816.
Sullenger B A and Cech T R (1993). *Science* 262:1566-1569.
Tycowski K T, et al. (1998). *Mol. Cell* 2:629-638.
Uhlenbeck O C (1987). *Nature (London)* 328:596-600.
Weinstein L B and Steitz J A (1999). *Curr. Opin. Cell Biol.* 11:378-384.
Wu F, et al. (1991). *Genes Dev.* 5:2128-2140.
Zapp M L and Green M R (1989). *Nature (London)* 342:714-716.
Zenzie-Gregory B, et al. (1993). *J Biol. Chem.* 268:15823-15832.
Zhang G, et al. (1996). *J. Cell Biol.* 135:9-18.
Zolotukhin A S and Felber B K (1999). *J. Virol.* 73:120-127.

What is claimed is:

1. A chimeric RNA molecule for delivering a ribozyme to the nucleolus of a cell, comprising a snoRNA or a portion thereof which retains the ability of a snoRNA to localize in the nucleolus of a cell, and a ribozyme which targets a sequence of the 5' LTR of HIV-1 RNA.

2. The RNA molecule of claim 1, wherein said snoRNA is a C/D box snoRNA.

3. The RNA molecule of claim 1, wherein said snoRNA comprises a C box and a D box.

4. The RNA molecule of claim 1, wherein said snoRNA is U16 snoRNA.

5. The RNA molecule of claim 4, wherein said ribozyme has replaced an apical loop of U16 snoRNA.

6. The RNA molecule of claim 5, wherein said ribozyme comprises bases 5-46 of SEQ ID NO:11.

7. The RNA molecule of claim 1, wherein said ribozyme is a hammerhead ribozyme.

8. An expression cassette comprising a coding sequence for the RNA molecule of claim 1.

9. The expression cassette of claim 8, further comprising an RNA pol III promoter sequence.

10. A cell comprising the RNA molecule of claim 1.

11. A method for inhibiting HIV replication in a HIV infected cell comprising introducing the RNA molecule of claim 1 into said HIV infected cell.

12. The method of claim 11, wherein said ribozyme localizes in the nucleolus of said HIV infected cell.

13. The method of claim 11, wherein said ribozyme comprises SEQ ID NO:11.

14. A method for treating a person infected with HIV comprising administering the RNA molecule of claim 1 to said person.

15. A method for inhibiting HIV replication in a HIV infected cell comprising introducing into said HIV infected cell a chimeric RNA molecule for delivering an HIV TAR RNA to the nucleolus of the cell, said chimeric RNA molecule comprising a snoRNA or a portion thereof which retains the ability of a snoRNA to localize in the nucleolus of the cell, and an HIV TAR RNA which binds HIV Tat protein.

16. The method of claim 15, wherein said HIV TAR RNA localizes in the nucleolus of said HIV infected cell.

17. The method of claim 15, wherein said HIV TAR RNA comprises SEQ ID NO:12.

18. A method for treating a person infected with HIV comprising administering to said person a chimeric RNA molecule for delivering an HIV TAR RNA to the nucleolus of the cell, said chimeric RNA molecule comprising a snoRNA or a portion thereof which retains the ability of a snoRNA to localize in the nucleolus of the cell, and an HIV TAR RNA which binds HIV Tat protein.

* * * * *

UNITED STATES PATENT AND TRADEMARK OFFICE
CERTIFICATE OF CORRECTION

PATENT NO. : 8,227,442 B2  
APPLICATION NO. : 12/835333  
DATED : July 24, 2012  
INVENTOR(S) : John J. Rossi et al.

Page 1 of 1

It is certified that error appears in the above-identified patent and that said Letters Patent is hereby corrected as shown below:

<u>TITLE PAGE, ITEM (56) OTHER PUBLICATIONS</u>

Page 2, left Col., line 39 under "Prislei et al.": "Acids Res." should be -- Nucleic Acids Res. --

<u>IN THE SPECIFICATION</u>

<u>BACKGROUND OF THE INVENTION</u>

Col. 1, line 56: "Hammarsk jold et al" should be -- Hammarskjold et al --

Col. 2, line 27: "HW" should be -- HIV --

<u>DETAILED DESCRIPTION OF THE INVENTION</u>

Col. 7, line 41: "Sad" should be -- Sa*c*l --

Signed and Sealed this  
Seventh Day of May, 2013

Teresa Stanek Rea  
*Acting Director of the United States Patent and Trademark Office*